US009518288B2

(12) United States Patent
Chagovetz et al.

(10) Patent No.: US 9,518,288 B2
(45) Date of Patent: Dec. 13, 2016

(54) METHODS AND COMPOSITIONS RELATED TO QUANTITATIVE, ARRAY BASED METHYLATION ANALYSIS

(75) Inventors: Alexander M. Chagovetz, Salt Lake City, UT (US); Steven M. Blair, Salt Lake City, UT (US); Randy L. Jensen, Salt Lake City, UT (US); Bryan J. Lowder, Holladay, UT (US)

(73) Assignee: University of Utah Research Foundation, Salt Lake City, UT (US)

( * ) Notice: Subject to any disclaimer, the term of this patent is extended or adjusted under 35 U.S.C. 154(b) by 1173 days.

(21) Appl. No.: 12/934,356

(22) PCT Filed: Apr. 13, 2009

(86) PCT No.: PCT/US2009/040378
§ 371 (c)(1),
(2), (4) Date: Dec. 16, 2010

(87) PCT Pub. No.: WO2009/134612
PCT Pub. Date: Nov. 5, 2009

(65) Prior Publication Data
US 2011/0281746 A1   Nov. 17, 2011

Related U.S. Application Data

(60) Provisional application No. 61/044,075, filed on Apr. 11, 2008.

(51) Int. Cl.
C40B 30/04   (2006.01)
C12Q 1/68    (2006.01)

(52) U.S. Cl.
CPC .......... *C12Q 1/6813* (2013.01); *C12Q 1/6827* (2013.01); *C12Q 1/6837* (2013.01); *C40B 30/04* (2013.01)

(58) Field of Classification Search
None
See application file for complete search history.

(56) References Cited

U.S. PATENT DOCUMENTS

| | | | |
|---|---|---|---|
| 5,033,291 | A | 7/1991 | Podoloff et al. |
| 5,244,636 | A | 9/1993 | Wait et al. |
| 5,338,430 | A | 8/1994 | Parsonage et al. |
| 5,408,873 | A | 4/1995 | Schmidt et al. |
| 5,525,466 | A | 6/1996 | Slovacek et al. |
| 5,627,922 | A | 5/1997 | Kopelman et al. |
| 5,641,658 | A | 6/1997 | Adams et al. |
| 5,677,196 | A | 10/1997 | Herron et al. |

(Continued)

FOREIGN PATENT DOCUMENTS

| | | |
|---|---|---|
| EP | 1208909 | 11/2001 |
| WO | WO 90/09576 | 8/1990 |

(Continued)

OTHER PUBLICATIONS

Stains et al. (Jul. 12, 2006) Journal of the American Chemical Society vol. 128 pp. 9761 to 9765.*

(Continued)

*Primary Examiner* — Christian Boesen
(74) *Attorney, Agent, or Firm* — Thorpe North & Western, LLP

(57) ABSTRACT

Disclosed are compositions and a method for detection of methylation based on quantitative arrays.

18 Claims, 12 Drawing Sheets

(56) References Cited

U.S. PATENT DOCUMENTS

| | | | |
|---|---|---|---|
| 5,678,448 | A | 10/1997 | Fullen et al. |
| 5,745,231 | A | 4/1998 | Groger et al. |
| 5,770,456 | A | 6/1998 | Holmes |
| 5,835,231 | A | 11/1998 | Pipino et al. |
| 5,929,332 | A | 7/1999 | Brown |
| 5,943,136 | A | 8/1999 | Pipino et al. |
| 5,973,316 | A | 10/1999 | Ebbesen et al. |
| 6,114,099 | A | 9/2000 | Liu et al. |
| 6,210,910 | B1 | 4/2001 | Wait et al. |
| 6,225,061 | B1 | 5/2001 | Becker et al. |
| 6,285,020 | B1 | 9/2001 | Kim et al. |
| 6,416,951 | B1 | 7/2002 | Schmidt et al. |
| 6,514,768 | B1 | 2/2003 | Guire et al. |
| 6,579,680 | B2 | 6/2003 | Frutos et al. |
| 6,589,740 | B2 | 7/2003 | Nakao et al. |
| 6,649,901 | B2 | 11/2003 | Thio et al. |
| 6,777,244 | B2 | 8/2004 | Pepper et al. |
| 6,893,822 | B2 | 5/2005 | Schweitzer et al. |
| 6,917,726 | B2 | 7/2005 | Levene et al. |
| 6,969,850 | B2 | 11/2005 | Staats |
| 7,013,054 | B2 | 3/2006 | Levene et al. |
| 7,171,331 | B2 | 1/2007 | Vock et al. |
| 7,181,122 | B1 | 2/2007 | Levene et al. |
| 7,272,079 | B2 | 9/2007 | Challener |
| 7,302,146 | B2 | 11/2007 | Turner et al. |
| 7,332,344 | B2 | 2/2008 | Morgan |
| 7,344,847 | B2 | 3/2008 | Hunt |
| 7,630,837 | B2 | 12/2009 | Eyre et al. |
| 7,741,105 | B2 | 6/2010 | Kim et al. |
| 7,745,143 | B2 | 6/2010 | Casasanta |
| 2001/0041339 | A1 | 11/2001 | Anderson et al. |
| 2002/0009394 | A1 | 1/2002 | Koster et al. |
| 2002/0081714 | A1 | 6/2002 | Jain et al. |
| 2002/0119485 | A1 | 8/2002 | Morgan |
| 2003/0017450 | A1 | 1/2003 | Oon et al. |
| 2003/0032076 | A1 | 2/2003 | Duffy et al. |
| 2003/0068446 | A1 | 4/2003 | Mirkin et al. |
| 2003/0087292 | A1 | 5/2003 | Chen et al. |
| 2003/0124594 | A1 | 7/2003 | Church et al. |
| 2003/0148401 | A1 | 8/2003 | Agrawal et al. |
| 2003/0170191 | A1 | 9/2003 | Imamura et al. |
| 2003/0173501 | A1 | 9/2003 | Thio et al. |
| 2003/0175702 | A1 | 9/2003 | Schweitzer et al. |
| 2003/0178641 | A1 | 9/2003 | Blair et al. |
| 2004/0029152 | A1 | 2/2004 | Ishida |
| 2004/0125190 | A1 | 7/2004 | Koyama |
| 2004/0180379 | A1 | 9/2004 | Van Duyne et al. |
| 2004/0224321 | A1 | 11/2004 | Nicolau et al. |
| 2005/0058774 | A1 | 3/2005 | Wada |
| 2005/0059014 | A1 | 3/2005 | Pawlak et al. |
| 2006/0099704 | A1 | 5/2006 | Predki et al. |
| 2007/0105100 | A1 | 5/2007 | Yoshii et al. |
| 2007/0161029 | A1* | 7/2007 | Li et al. ............... 435/6 |
| 2007/0202478 | A1 | 8/2007 | Al-Obaidi et al. |
| 2007/0264653 | A1* | 11/2007 | Berlin et al. ............ 435/6 |
| 2008/0032301 | A1 | 2/2008 | Rank et al. |
| 2008/0039339 | A1 | 2/2008 | Hassibi et al. |
| 2008/0297757 | A1 | 12/2008 | Hahn |
| 2009/0042735 | A1 | 2/2009 | Blair et al. |
| 2010/0256016 | A1 | 10/2010 | Blair et al. |

FOREIGN PATENT DOCUMENTS

| | | |
|---|---|---|
| WO | WO/91/06862 | 5/1991 |
| WO | WO 92/21976 | 12/1992 |
| WO | WO93/14393 | 7/1993 |
| WO | WO 94/25850 | 11/1994 |
| WO | WO 97/35181 | 9/1997 |
| WO | WO 99/37996 | 7/1999 |
| WO | WO 99/49937 | 10/1999 |
| WO | WO 2007/094817 | 8/2007 |
| WO | WO 2009/023716 | 2/2009 |
| WO | WO2009/149125 | 12/2009 |

OTHER PUBLICATIONS

Yegnasubramanian et al. (Feb. 9, 2006) Nucleic Acids Research vol. 34 article e19 pp. 1 to 14.*
Guiller et al; Linkers and Cleavage Strategies in Solid-Phase Organic Synthesis and Combinatorial Chemistry; Chemical Reviews; May 6, 2000; pp. 2091-2157; vol. 100.
Bauer et al; Biological Applications of High Aspect Ratio Nanoparticles; Journal of Materials Chemistry; Jan. 14, 2004; pp. 517-526; vol. 14.
Murphy et al; Probing Single-Stranded DNA Conformational Flexibility Using Fluorescence Spectroscopy; Biophysical Journal; Apr. 2004; pp. 2530-2537; vol. 86.
U.S. Appl. No. 12/191,134, filed Aug. 13, 2008; Alexander Chagovetz; office action issued Sep. 9, 2011.
Dodge et al.; A Microfluidic Platform Using Molecular Beacon-Based Temperature Calibration for Thermal Dehybridization of Surface-Bound DNA; Anal. Chem. 2004; vol. 76; pp. 1778-1787.
U.S. Appl. No. 11/633,980, filed Dec. 4, 2006; Alexander M. Chagovetz; office action issued Apr. 28, 2011.
U.S. Appl. No. 12/042,516, filed Mar. 5, 2008; Steven M. Blair; office action issued Apr. 29, 2011.
U.S. Appl. No. 12/603,242, filed Oct. 21, 2009; Steven M. Blair; office action dated Aug. 23, 2012.
U.S. Appl. No. 12/042,516, filed Mar. 5, 2008; Steven M. Blair; office action dated Oct. 9, 2012.
U.S. Appl. No. 12/793,883, filed Jun. 4, 2010; Steven M. Blair; office action dated Nov. 9, 2012.
Liu et al; Biosensing Based upon Molecular Confinement in Metallic Nanocavity Arrays; Proceedings of the SPIE—The International Society for Optical Engineering SPIE-INT. Soc. Opt. Eng USA; Apr. 11, 2005; vol. 5703, No. 1.
Airola et al; Second-Harmonic Generation from an Array of Subwavelength Metal Apertures; Second-Harmonic Generation from Subwavelength Metal Apertures; Journal of Optics. A; Feb. 1, 2005; pp. S118-S123; vol. 7, No. 2.
Tang et al; C-Shaped Nanoaperture-Enhanced Germanium Photodetector; Optics Letters; posted online Feb. 16, 2012; pp. 1519-1521; vol. 31, No. 10.
K. Koerkamp et al.; Strong Influence of Hole Shaped on Extraordinary Transmission Through Periodic Arrays of Subwavelength Holes; Physical Review Letters; May 1, 2004; vol. 92, No. 18.
Heybel et al; Crucial Role of the Adhesion Layer of the Plasmonic Fluorescence Enhancement; ACS Nano; 2009; pates 2043-2048; vol. 3, No. 7.
U.S. Appl. No. 12/793,883, filed Jun. 4, 2010; Steven M. Blair; office action issued Apr. 5, 2012.
Adey, N. B.; Lei, M.; Howard, M. T.; Jensen, J. D. ; Mayo, D. A.; Butel, D. L., Coffin, S. C.; Moyer, T. C., Slade, D. E., Spute, M. K., Hancock, A. M., Eisenhoffer, G. T., Dalley, B. K. and McNeely, M. R. "Gains in sensitivity with a device that mixes rnicroarray hybridization solution in a 25-mm-thick chamber." *Anal. Chem.* 74:6413-6417 (2002).
Altug, H. and Vuckovic, J. "Polarization control and sensing with two-dimensional coupled photonic crystal mitrocavity arrays" *Optics Letters* 30(9):982-984 (May 2005).
Attridge, J.W., Daniels, P. B., Deacon, J. K., Robinson, G. A. and Davidson, G. P. "Sensitivity enhancement of optical immunosensors by the use of a surface plasmon resonance fluoroimmunoassay" *Biosensors and Bioelectronics* 6:201-214 (1991).
Bhanot, G, Louzoun, Y., Zhu, J. and DeLisi, C. "The importance of thermodynamic equilibrium for high throughput gene expression arrays." *Biophys. J.* 84:124-135 (2003).
Bianchi, N. , Rustigliano, C. , Tomassetti, M. , Feriotto; G. , Zorzato, F. and Gambari, R. "Biosensor technology and surface plasmon resonance for real-time detection of HIV-1 genomic sequences amplified by polymerase chain reaction." *Clinical and Diagnostic Virology* 8:199-208 (1997).
Bishop, J. et al. "Competitive Displacement of DNA during Surface Hybridization." *Biophy. J.* 91(1):L10-L12 (Jan. 2007a).
Bishop, J., A. Chagovetz, and S. Blair "Competitive displacement: a sensitive and selective method for the detection of unlabeled molecules." *Opt. Express* 15:4390-4397 (2007b).

(56) References Cited

OTHER PUBLICATIONS

Bishop, J., S. Blair, and A. Chagovetz. "Convective flow effects on DNA biosensors." *Biosens. Bioelectron.* 22:2192-2198 (2007c).
Bishop, J., Blair, S. and Chagovetz, A. M. "A competitive kinetic model of nucleic acid surface hybridization in the presence of point mutants." *Biophys. J.* 90:831-840 (2006).
Blair, S. and Chen, Y. "Resonant-enhanced evanescent-wave fluorescence biosensing using cylindrical optical cavities." *Applied Optics* 40:570-582 (2001).
Boyd, R W. and Heebner, J. E. "Sensitive disk resonator photonic biosensor." *Applied Optics-OT* 40:5142-5747 (2001).
Chan, V., D. J. Graves, P. Fortina, and S. E. McKenzie. "Absorption and surface diffusion of DNA oligonucleotides at liquid! solid interfaces." *Langmuir* 13:320-329 (1997).
Chechetkin, V. R. "Two-compartment model for competitive hybridization on molecular biochips." *Phys. Lett. A.* 360:491-494 (2007).
Dai, H., M. Meyer, S. Stepaniants, M. Ziman, and R. Stoughton "Use of hybridization kinetics for differentiating specific from non-specific binding to oligonucleotide microarrays." *Nucleic Acids Res.* 30:e86-1-8 (2002).
Dandy, D. S., P. Wu, and D. W. Grainger. "Array feature size influences nucleic acid surface capture in DNA microarrays." *Proc. Natl. Acad. Sci.* USA. 104:8223-8228 (2007).
Ditlbacher, H.; Felidj, N., Krenn, J. R., Lambprecht, B., Leitner, A. and Aussenegg, F. R. "Electromagnetic intereaction of fluorophores with designed 2D silver nanoparticle arrays." *Applied Physics B* 73:373 (2001).
Elanko, N. and Jeffery, S. "Mutation analysis of PTPN11 in Noonan syndrome by Wave." *Methods Mol Med.* 126:97-111 (2006).
Erickson, D., X. Liu, U. Krull, and D. Li. "Electrokinetically controlled DNA hybridization microfluidic chip enabling rapid target analysis." *Anal. Chem.* 76:7269-7277 (2004).
Erickson, D., D. Li, and U. Krull. "Modeling of DNA hybridization kinetics for spatially resolved biochips." *Anal. Biochem.* 317: 186-200 (2003).
Fish, D. J., M. T. Horne, R. P. Searles, G. P. Brewood, and A. S. Benight "Multiplex SNP discrimination." *Biophys. J.* 92:L89-L91 (2007).
Gao, Y., L. K. Wolf, and R. M. Georgiadis. "Secondary Structure effects on DNA hybridization kinetics: a solution versus surface comparison." *Nucleic Acids Res.* 34:3370-3377 (2006).
Hagan, M. F., and A. K. Chakraborty. "Hybridization dynamics of surface immobilized DNA." *J. Chem. Phys.* 120:4958-4968 (2004).
Hall TA, Budowle B, Jiang Y, Blyn L, Eshoo M, Sannes-Lowery KA, Sampath R, Drader JJ, Hannis JC, Harrell P, Samant V, White N, Ecker DJ, Hofstadler SA "Base composition analysis of human mitochondrial DNA using electrospray ionization mass spectrometry: a novel tool for the identification and differentiation of humans." *Anal Biochem*, 344(1):53-69 (Sep. 1, 2005).
Halperin, A., Buhot, A. and Zhulina E. B. "Sensitivity, specificity, and the hybridization isotherms of DNA chips." *Biophys. J.* 86:718-730 (2004).
Halperin, A., Buhot, A. and Zhulina, E. B. "On the hybridization isotherms of DNA microarrays: the Langmuir model and its extensions." *J. Phys.: Condens. Matter.* 18:S463-S490 (2006).
Held, G. A., G. Grinstein, and Y. Tu. "Relationship between gene expression and observed intensities in DNA microarrays—a modeling study." *Nucleic Acids Res.* 34:e70 (2006).
Henry, M. R. , Stevens, P. W., Sun, J. and Kelso, D. M. "Real-time measurements of DNA hybridization on microparticles with fluorescence resonance energy transfer." *Analytical Biochemistry* 276:204-214 (1999).
Horne MT, Fish DJ, Benight AS "Statistical thermodynamics and kinetics of DNA Multiplex hybridization reactions." *Biophys J.* 91(11):4133-53 (2006).
Ilic, B., Yang, Y., Aubin, K., Reichenbach, R., Krylov, S. and Craighead, H. G. "Enumeration of DNA molecules bound to a nanomechanical oscillator." *Nano Letters* 5:925-929 (2005).

Jiang Y, Hall TA, Hofstadler SA, Naviaux RK "Mitochondrial DNA mutation detection by electrospray mass spectrometry." *Clin Chem.* 53(2):195-203 Epub (Dec. 7, 2006).
Kim, J., S. Doose, H. Neuweiler, and M. Sauer "The initial step of DNA hairpin folding: a kinetic analysis using fluorescence correlation spectroscopy." *Nucleic Acid Res.* 34:2516-2527 (2006).
Kleibl, Z., O. Havranek, and J. Prokopcova "Rapid detection of CAA/CAG repeat polymorphism in the AIB1 gene using DHPLC. "*J Biochem Biophys Methods. Epub* ahead of print—(2006).
Lee, N. H., and A. I. Saeed. "Microarrays: an overview." *Methods Mol. Biol.* 353:265-300 (2007).
Lee, H. J., A. W. Wark, Y. Li, and R. M. Corn "Fabricating RNA microarrays with RNA-DNA surface ligation chemistry." *Anal Chem.* 77(23):7832-7 (2005).
Levicky, R., and A. Horgan. "Physicochemical perspectives on DNA microarray and biosensor technologies." *Trends Biotechnol.* 23:143-149 (2005).
Li, Y., A. W. Wark, H. J. Lee, and R. M. Corn. "Single-nucleotide polymorphism genotyping by nanoparticle-enhanced surface plasmon resonance imaging measurements of surface reactions." *Anal Chem.* 78(9):3158-64 (2006).
Liedberg, B., Nylander, C. and Lundström, I. "Surface plasmon resonance for gas detection and biosensing," *Sensors and Actuators* 4:299-304 (1983).
Liu, Y. and Blair, S. "Fluorescence enhancement from an array of sub-wavelength I metal apertures." *Optics Letters* 28:507-509 (2003).
Livshits, M. A., and A. D. Mirzabekov. "Theoretical analysis of the kinetics of DNA hybridization with gel-immobilized oligonucleotides." *Biophys. J.* 71:2795-2801 (1996).
Malicka, J., Gryczynski, I. and Lakowicz, J. R. "DNA hybridization assays using metal-enhanced fluorescence." *Biochemical and Biophysical Research Communications* 306:213-218 (2003).
Markham, N. R. and M. Zuker "DINAMelt web server for nucleic acid melting prediction." *Nucleic Acids Res.* 33:W577-W581 (2005).
Marotta, R., J. Chin, A. Quigley, S. Katsahanis, R. Kapsa, E. Byme, and S. Collins "Diagnostic screening of mitochondrial DNA mutations in Australian adults 1990-2001." *Intern Med J.* 34(1-2):10-9 (2004).
Moerner, W. E. and Fromm, D. P. "Methods of single-molecule fluorescence spectroscopy and microscopy." *Review of Scientific Instruments* 74:3597-3619.
Myszka, D. G., X. He, M. Dembo, T. A. Morton, and B. Goldstein. "Extending the range of rate constants available from BIACORE: interpreting mass transport-influenced binding data." *Biophys. J.* 75:583-594 (1998).
Korlach et al., "Selective aluminum passivation for targeted immobilization of single DNA polymerase molecules in zero-mode waveguide nanostructures," pNAS, Jan. 29, 2008, pp. 1176-1181, vol. 105, No. 4.
Mutin et al., "Selective surface modification of SiO2—TiO2 supports with phosphonic acids," Chem. Mater. 2004, pp. 5670-5675, vol. 16.
Marthandam et al., "Plasmonic bragg reflectors for enhanced extraordinary optical transmission nanohole arrays ina gold film," Optics Express, Oct. 1, 2007, pp. 12995-13002, vol. 15, No. 20.
Feng et al., "Optical transmission through single subwavelegth apertures using prism coupled input of laser light annular intensity profile," Optics Express, Dec. 24, 2007, pp. 17863-17873, vol. 15, No. 16.
Louarn et al., "Prediction of the transmitted light through a nanoaperture of SNOM Probes", Proceedings of the COMSOL Users Conference 2006, 4 pages, Paris.
Heng et al., :Nano-aperture array based optical imaging system on a microfluidic chip, IEEE, 2006, 2 pages.
Bargiel et al, "A micromachined silicon-based probe for a scanning near-field optical microscope on-chip," Institute of Physics Publishing, Measurement Science and Technology, 2006, pp. 32-37, vol. 17.
Archer et al., "Fabrication and characterization of silicon microfunnels and tapered micro-channels for stochastic sensing applications," Sensors 2008, pp. 3848-3872, vol. 8.

(56) References Cited

OTHER PUBLICATIONS

Verhagen et al., "Nanofucusing in laterally tapered plasmonic waveguides," Optics Express, Jan. 7, 2008, pp. 45-57, vol. 16, No. 1.
Szunerits et al., "Fabrication of a sub-micrometer electrode array: elecrochemical characterization and mapping of electroactive species by confocal raman microspectroscopy," Electroanalysis 2003, pp. 548-555, vol. 15 No. 5-6.
Liu et al., "Biosensing based upon molecular confinement in metallic nanaocavity arrays," IEEE, 2004 pp. 31-32.
Haes et al., "A nanoscale optical bioserisor: sensitivity and selectivity of an approach based on the localized surface plasmon resonance spedinscopy of triangular silver nanoparticals," J. Am. Chem Soc 2002, 124, 10596-10604.
Chen, "Enhancement of the resolution of surface plasmon resonance biosensors by control of the size and distribution of nanoparticles," Optical Letters, Jun. 15, 2004, pp. 1390-1392, vol. 29, No. 12.
Liu et al., "The enhancement effect of gold nanoparticles as a surface modifier on DNA sensor sensitivity," Biochemcial and Biophysical Research Communications 311 (2004), pp. 3-7.
Song, "Ultrahigh-Q Nanocavity based on photonic-crystal double heterostructure," Quantum Electronics and Laser Science Conference, 2005, pp. 407-409.
Levene, "Zero-mode waveguides for single-molecular analysis at high concentrations," Science, Jan. 31, 2003, vol. 299.
Martin-Moreno et al., "Optical transmission through circular hole arrays in optically thick metal films,"Optics Express, Aug. 9, 2004, pp. 3619-3628, vol. 12; No. 16.
Blair, et al., "Enhancement of molecular fluorescence by metallic nanocavities," Proc of SPIE vol. 5927, 2005, 5 pages.
Ngeh-Ngwainbi, J., Suleiman, A. A. and Guilbault, G. G. "Piezoelectric crystal biosensors." *Biosensors & Bioelectronics* 5:13-26 (1990).
Oberacher, H., H. Niederstatter, and W. Parson "Liquid chromatography-electrospray ionization mass spectrometry for simultaneous detection of mtDNA length and nucleotide polymorphisms." *Int J Legal Med*. 121(1):57-67 (2007).
Oh, S.J., B.J. Hong, K.Y. Choi, and J. W. Park. "Surface modification for DNA and protein microarrays. OMICS:" *J. Integra. Biol.* 10:327-343 (2006).
Okamoto, T., Yamaguchi, I. and Kobayashi, T. "Local plasmon sensor with gold colloid monolayers deposited upon glass substrates." *Optics Letters* 25:372-374 (2000).
Okoniewski, M. J., and C. J. Miller. "Hybridization interactions between probesets in short oligo microarrays lead to spurious correlations." *BMC Bioinformatics*. 7:276(2006).
Peterson, A. W., L. K. Wolf, and R. M. Georgiadis. "Hybridization of mismatched or partially matched DNA at surfaces." *J. Am. Chem. Soc.* 124:14601-14607 (2002).
Plowman, T. E., Reichert, W. M., Peters, C. R., Wang, H. K., Christensen, D. A. and Herron, J. N. "Femtomolar sensitivity using a channel-etched thin film waveguide fluoroimmunosensor" *Biosensors and Bioelectronics* 11:149-160 (1996).
Plum, G. E. and K. J. Breslauer "Fluorescence energy transfer monitored competitive equilibria of nucleic acids: applications in thermodynamics and screening." *Biopolymers* 61:214-223 (2002).
Podder, M., W. J. Welch, R. H. Zamar, and S. J. Tebbutt. "Dynamic variable selection in SNP genotype autocalling from APEX microarray data." *BMC Bioinformatics* 30:7:521 (2006).
Provenzano, M., and S. Mocellin. "Complementary techniques: validation of gene expression data by quantitative real time PCR." *Adv. Exp. Med. Biol.* 593:66-73 (2007).
Reichert, W. M. "Evanescent detection of adsorbed protein films: assessment of optical considerations for absorbance and fluorescence spectroscopy at the crystal solution and polymer solutions interfaces." *Critical Reviews in Biocompatability* 5:173 (1989).

Riccelli, PV, Hall, TS, Pancoska P, Mandell KE, Benight AS. "DNA sequence context and multiplex hybridization reactions: melting studies of heteromorphic duplex DNA complexes." *J Am Chem Soc*. 125(1):141-50 (Jan. 8, 2003).
Riccelli PV, Merante F, Leung KT, Bortolin S, Zastawny RL, Janeczko R, Benight AS. "Hybridization of single-stranded DNA targets to immobilized complementary DNA probes: comparison of hairpin versus linear capture probes." *Nucleic Acids Res*. 15:29(4):996-1004 (2001).
Rindzevicius, T., Alaverdyan, Y. Dahlin, A., Hook, F., Sutherland, D. S. and Kall, M. "Plasmonic sensing characteristics of single nanometric holes." *Nano Letters* 5:2335-2339 (2005.
Roederer, E. and Bastiaans, G. J. "Microgravimetric immunoassay with piezoelectric crystals." *Analytical Chemistry* 55: 2333-2336 (1983).
Rudi, K., M. Zimonja, and B. Skanseng. "Quencher extension for single nucleotide polymorphism quantification in bacterial typing and microbial community analyses." *Methods Mol Biol*. 345:111-7 (2006).
Sekar, M. M. A., W. Bloch, and P. M. S. John. "Comparative study of sequence-dependent hybridization kinetics in solution and on microspheres." *Nucleic Acids Res*. 33:366-375 (2005).
Sorokin, N. V., D. Y. Yurasov, A. L. Cherepanov, J.M. Kozhekbaeva, V. R. Chechetkin, O. A. Gran, M. A. Livshits, T. V. Nasedkina, and A. S. Zasedatelev. "Effects of external transport on discrimination between perfect and mismatch duplexes on gel-based oligonucleotide microchips." *J. Biomol. Struct. Dyn*. 24:571-578 (2007).
Situma, C., M. Hashimoto, and S. A. Soper. "Merging microfluidics with microarray-based bioassays." *Biomol. Eng*. 23:213-23 1 (2006).
Stimpson, D. I., Hoijer, J.V., Hsieh, W. T., Jou, C., Gordon, J., Theriault, T., Gamble, R., and Baldeschwieler, J.D. "Real-time detection of DNA hybridization and melting on oligonucleotide arrays by using optical wavegides." *Proceedings of the National Academy of Science* 92:6379-6383 (1995).
Storhoff, J. J., Marla, S. S., Garimella, V. and Mirkin, C. A. "Labels and detection methods." *Springer* 147-174 (2005).
Taitt, C. R., G. P. Anderson, and F. S. Ligler. "Evanescent wave fluorescence biosensors." *Biosens. Bioelectron*. 20:2470-2487 (2005).
Taton, T. A., Mirkin, C. A. and Letsinger, R. L. "Scanometric DNA array detection with nanoparticle probes" *Science* 289:1757-1760 (2000).
Tawa, K., D. Yao, and W. Knoll. "Matching basepair number dependence of the kinetics of DNA-DNA hybridization studied by surface plasmon fluorescence pectroscopy." *Biosens. Bioelectron*. 21:322-329 (2005).
Tsujikawa, K., M. Tsujikawa, H. Watanabe, N. Maeda, Y. Inoue, T. Fujikado, and Y. Tano. "Allelic homogeneity in Avellino corneal dystrophy due to a founder effect." *J Hum Genet*. 52(1):92-7 (2007).
Vaisocherova, H., Zitova, A., Lachmanova, M., Stepanek, J., Karlikova, S., Liboska, R., Rejman, D., Rosenberg, I. and Homola, J. "Investigating oligonucleotide hybridization at subnanomolar level by surface plasmon resonance biosensor method." *Biopolymers* 82:394-398 (2005).
Wang, Y., C. Barbacioru, F. Hyland, W. Xiao, K. L. Hunkapiller, J. Blake, F. Chang, C. Gonzalez, L. Zhang, and R. R. Samaha. "Large-scale real-time PCR validation on gene expression measurements from two commercial long-oligonucleotide microarrays." *BMC Genomics* 7:59 (2006).
Wark, A.W., Lee, H. J. and Corn, R. M. "Long-range surface plasmon resonance imaging for bioaffinity sensors." *Analytical Chemistry* 77:3904-3907 (2005).
Weis, B. K. "Standardizing global gene expression analysis between laboratories and across platforms." *Nat. Methods*. 2:35 1-356 (2005).
Wong, L. J. and R. G. Boles. "Mitochondrial DNA analysis in clinical laboratory diagnostics." *Clin Chim Acta*. 354(1-2):1-20 (2005).
Wong, L. J. "Comprehensive molecular diagnosis of mitochondrial disorders: qualitative and quantitative approach." *Ann N Y Acad Sci*. 1011:246-58 (2004).

(56) References Cited

OTHER PUBLICATIONS

Wren, J. D., A. Kullcami, J. Joslin, R. A. Butow, R. G. Harold. "Cross-hybridization on PCR-spotted microarrays." IEEE Eng. Med. Biol. 21:71-75 (2002).
"Schechter, Bright new World," New Scientist, vol. 178, p. 31-33 (2003).
Yguerabide et al., "Light-stattering submicroscopic particles as highly fluorescent analogs and their use as tracer labels in clinical and biological applications," Anal. Biochem.. vol. 262, No. 2, (Sep. 1998) p. 137-156.
Hirsch et al., "A whole blood imnunoassay using gold nanoshells," Anal. Chem.., vol. 75, (2003) p. 2377-2381.
Wokaun et al., "Energy transfer in surface enhanced luminescence," J. Chem. Phys., vol. 79, No. 1, p. 509-514 (1983).
Malicka et al., "Effects on fluorophone-to-silver distance on the emission of cyanine-dye-labeled obligonucleotides," Anal. Biochem., vol. 315, p. 57-66 (2003).
Kneipp et al., "Extremely large enhancement factors in surface-enhanced Raman scattering for molecules on colloidal gold clusters," Appl. Spectros., vol. 52, p. 1493-1497 (1998).
Shalaev et al., "Optical properties of self-affine thin films," Phys. Rev. B, vol. 54, p. 8235-8242 (1996).
Ditlbacher et al., "Electromagnetic interaction of fluorophores with designed 2D silver nanoparticle arrays," Appl. Phys. B, vol. 73, (2001) p. 373-377.
Felidj et al., "Optimized surface-enhanced Raman scattering on gold nanoparticle arrays." Appl. Phys. Lett. vol. 82, No. 18, p. 3095-3097 (2003).
Ebbeson et al., "Extraordinary optical transmission through sub-wavelength hole arrays," Nature, vol. 391, p. 667-669 (1998).
Lezec et al., "Diffracted evanescent wave model for enhanced and suppressed optical transmission through subwavelength hole arrays," Optics Express, vol. 12, No. 16, p. 3629-3651 (2004).
Avrutsky et al., "Surface-plasmon-assisted resonant tunneling of light through a periodically corrugated thin metal film," Opt. Lett., vol. 25, p. 595-597 (2000).
Sarychev et al., "Resonance transmittance through a metal film with subwavelength holes," IEEE J. Quantum Election, vol. 38, p. 956-963 (2002).
Liu et al., "Fluorescence transmission through 1-D and 2-D periodic metal films," Opt. Express, vol. 12, No. 16, p. 3686-3693 (2004).
Rigneault et al., "Enhancement of single-molecule fluorescence detection in subwavelength apertures," Physical Review Letters 95, p. 117401 (2005).
Wenger et al., "Single-molecule fluorescence in rectangular nano-apertures," Optics Express, vol. 13, p. 7035-7044 (2005).
Liu et al., "Enhanced fluorescence transduction properties of metallic nanocavity arrays," IEEE Journal of Selected Topics in Quantum Electronics, vol. 11, p. 778-784 (2005).
Maron et al., "Impact of laboratory molecular diagnosis on contemporary diagnostic criteria for genetically transmitted cardiovascular diseases: hypertropic cardiomyopathy, long-QT syndrome, and Marfan syndrome," Circulation, vol. 98, p. 1460-1471 (1998).
Hacia, "Resequencing and mutational analysis using obligonucleotide microarrays," Nature Genetics, vol. 21, p. 42-47 (1999).
Moerner et al., "Methods of single-Molecule fluorescence spectroscopy and microscopy," Review of Scientific Intruments, vol. 74, p. 3597-3619 (2003).
Belosludtsev et al., "Organism identification using a genome sequence independent universal microarray probe set," Biotechniques, vol. 37, p. 654-660 (2004).
Saluz et al., "Fundamentals of DNA-chip/array technology for comparative gene-expression analysis," Current Science, vol. 83, p. 829-833 (2002).
Chou et al., "Nanoimprint lithography," Journal of Vacuum Science and Technology B, vol. 14, p. 4129-4133 (1996).
Prime et al., "Adsorption of proteins onto surfaces containing end-attached oligo(ethylene oxide): a model system using self-assembled monolayers," Journal the American Chemical Society, vol. 115, p. 10714-10721 (1993).
Disley et al., "Covalent coupling of immunoglobulin G to self assembled monolayers as a method for immobilizing the interfacial-recognition layer of a surface Plasmon resonance immunosensor," Biosensors and Bioelectronics, vol. 13, p. 1213-1225 (1998).
Smolyaninov et al., "Near-field optical microscopy of two-dimensional photonic and plasmonics crystals," Physical Review B, vol. 59, p. 2454-2460 (1999).
Ermuschev et al., "Surface enhancement of local optical fields and the lightning-rod effect," Quantum Electronics, vol. 23, p. 435-440 (1993).
Gruhlke et al., "Surface-plasmon cross-coupling in molecular fluorescence near a corrugated thin metal film," physical Review letters, vol. 56, p. 2838-2841 (1986).
Gruhlke et al., "Optical emission from coupled surface plasmons," Optics letters, vol. 12, p. 364-366 (1987).
Herron et al., "Planar waveguide biosensors for nucleic acid hybridization reactions," Proceedings SPIE, vol. 3913, p. 177-484 (2000).
Myszka et al., "The range of rate constants available from BIACORE: interpreting mass transport-influenced binding data," Biophysical Journal, vol. 75, p. 583-594 (1998).
Dai et al., "Use of hybridization kinetics for differentiating specific from non-specific binding to oligonucleotide microarrays," Nucleic Acids Research, vol. 30 (2002) e86.
Heaton et al., "Electrostatic surface Plasmon resonance: direct electric field-induced hybridization and denaturation in monolayer nucleic acid films and label-free discrimination of the base mismatches," Proceedings of the National Academy of Sciences, vol. 98, p. 3701-3704 (2001).
"Su et al., heterogeneous hybriditation on indium tin oxide with and without an applied potential," Electrophoresis, vol. 23, p. 1551-1557 (2002).
Lee et al., "Nanoscale two-dimensional patterning on Si(001) by large-area interferometric lithography and anisotropic wet etching," Journal of Vacuum Science & Technology B, vol. 22, p. 1949-1952 (2004).
Murray et al., "Transition from localized surface Plasmon resonance to extended surface Plasmon-polatiton as metallic nanopartiales merge to from a periodic hole array," Physical Review B, vol. 69, p. 165407 (2004)
Thio et al., "Enhanced light transmission-through a single subwavelength aperture," Optic Letter, vol. 26, p. 1972-1974 (2001).
Malicka et al., "DNA hybridization assays using metal-enhanced fluorescence," Biochemical and Biophysical Research Communications, vol. 306, p. 213-218 (2003).
Blanco et al., "Spontaneous light emission in complex nanostructures," Physical Review B, vol. 69, p. 205414 (2004).
Nahata et al., "Enhanced nonlinear optical conversion using periodically nanostructured metal films," Optics Letters, vol. 28, p. 423-425 (2003).
Fleischmann et al., "Raman spectra of pyridine adsorbed at a silver electrode," Chemical Physics Letters, vol. 26, p. 163-166 (1974).
Craighead et al., "Optical absorption of small metal particles with adsorbed dye coats", Optics Letters, vol. 6, 248-250 (1981).
Ditlbacher et al., "Electromagnetic intereaction of fluorophores with designed 2D silver nanoparticle arrays," Applied Physics B, vol. 73, p. 373-377 (2001).
Bruchez et al., "Semiconductor nanocrystals as fluorescent biological labels," Science, vol. 281, p. 2013-2016 (1998).
Chan et al., "Quantum dot bioconjugates for ultrasensitive nonisotropic detection," Science, vol. 281, p. 2016-2018 (1998).
Mandavi et al., "Modeling Fluorescence Enhancement from Metallic Nanocavities", Plasmonics, vol. 2, p. 129-141 (2007).
Gerard et al., "Nanoaperture-enhanced fluorescence: Towards higher defection rates with metals," Physical Review B, vol. 77, 045413 (2008).
Yonzon, C. R. , Jeoung, E. , Zou, S., Schatz, G. C., Mrksich, M., and Duyne, R. P. V. "A comparative analysis of localized and propagating surface plasmon resonance sensors: the binding of

(56) References Cited

OTHER PUBLICATIONS

Concanavalin A toMonosaccharide functionalized self-assembled monolayer." *Journal of the American Chemical Society* 126:12669-12676 (2005).

Zhang, Y., Hammer, D. A. and Graves, D. J. "Competitive hybridization kinetics reveals unexpected behavior patterns." *Biophysical Journal* 89:2950-2959 (2005).

Zhou, Y., Laybourn, P. J., Magill, J. V. and L' Rue, R. M. D. "An evanescent fluorescence biosensor using ionexchanged buried waveguides and the enhancement of peak fluorescence." *Biosensors and Bioelectronics* 6:595-607 (1991).

C. Genet "Fano-type interpretation of red shifts and red tails in hole array transmission spectra"; Science Direct, Jul. 15, 2003; accepted Jul. 18, 2003.

Heykel Aouani et al; Crucial Role of the Adhesion Layer on the Plasmonic Fluorescence Enhancement; ACS Nano, vol. 3, No. 7, 2043-2048; 2009.

Xiaojin Jiao et al; "Localization of Near-Field Resonance in Bowtie Antennae: Influence of Adhesion Layers"; Plasmonics (2009) 4:37-50.

Pipino; "Ultrasensitive Surface Spectroscopy with a Miniature Optical Resonator"; Physical Review Letters; Oct. 11, 1999.

Heise, et al; "Attenuated total reflection mid-infrared spectroscopy for clinical chemistry applications using silver halide fibers"; Sensors and Actuators B 51 (1998) 84-91.

Keiki-Pua et al.; "Development of a Porous Silicon Based Biosensor"; Mat. Res. Soc. Symp. Proc. vol. 536; 1999 Materials Research Society.

Bammler, et al.; "Standardizing global gene expression analysis between laboratories and across platforms"; Nature Methods, vol. 2 No. 5; May 2005.

Abel et al. (Analytical Chemistry, 1996, 68, 2905-2912).

Stimpson et al. (Genetic Analysis: Biomolecular Engineering, 1996, 13, 73-80).

U.S. Appl. No. 12/603,242, filed Oct. 21, 2009; Steven M. Blair; office action dated Dec. 26, 2012.

\* cited by examiner

FIGURE 3
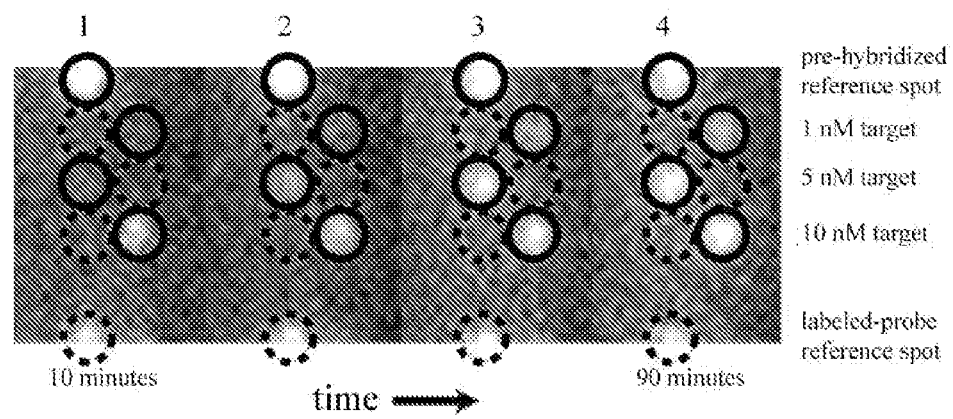
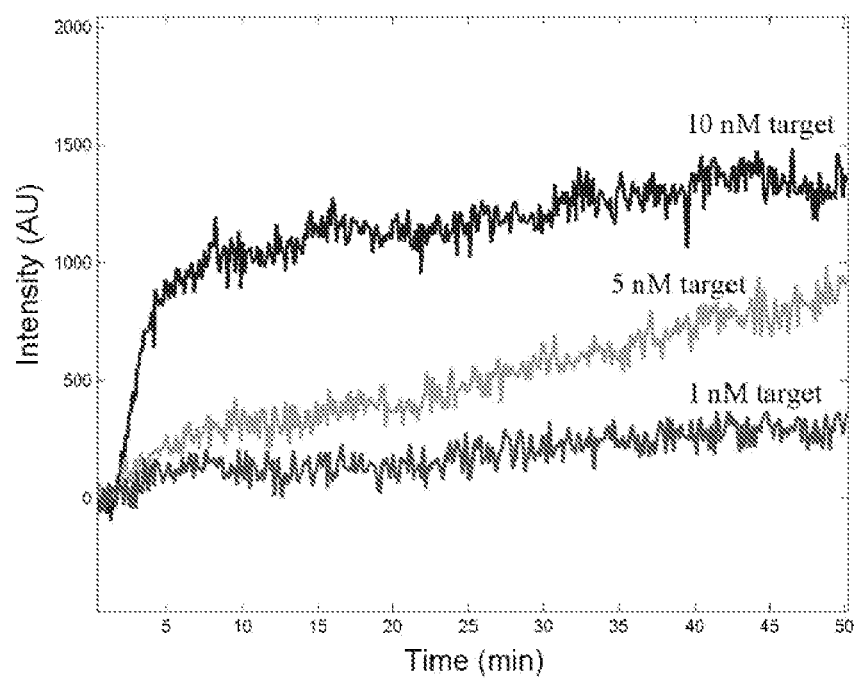

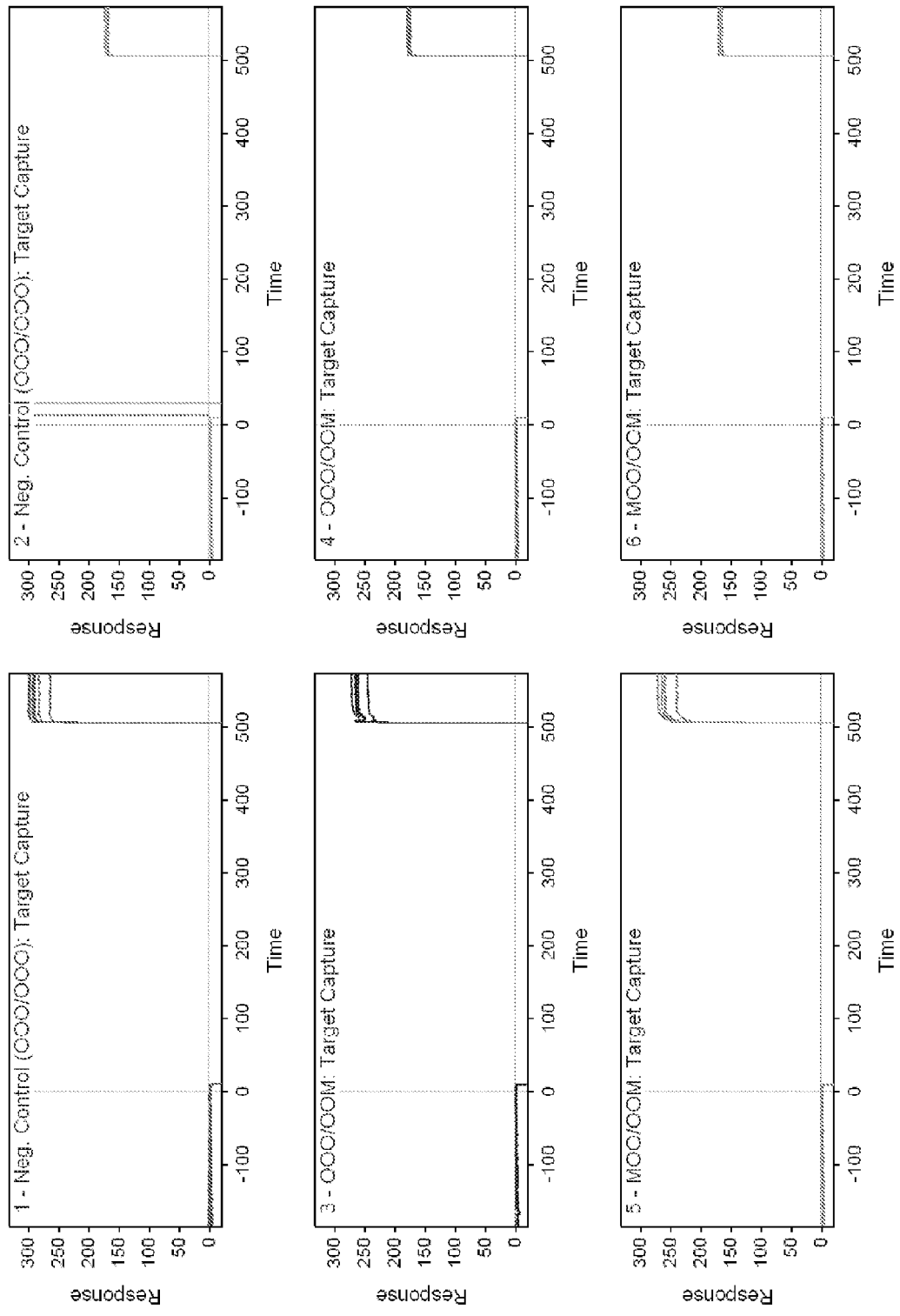

METHODS AND COMPOSITIONS RELATED TO QUANTITATIVE, ARRAY BASED METHYLATION ANALYSIS

CROSS-REFERENCE TO RELATED APPLICATIONS

This is a nationalization of PCT/US2009/040378, filed Apr. 13, 2009; which claims benefit of U.S. Provisional Application No. 61/044,075, filed Apr. 11, 2008, which is hereby incorporated herein by reference in its entirety.

BACKGROUND OF THE INVENTION

The disclosed invention is in the general field of nucleic acid detection, and specifically in the field of detection of methylation of nucleic acids using quantitative analysis.

Successful implementation of the promise of personalized medicine lies at the crossroads of performing accurate, rapid genetic analyses with the interpretation of the test results to diagnose and treat individual patients. The critically important parameter among these qualities is the accuracy of diagnostic test results.

DNA methylation is a ubiquitous mechanism of epigenetic regulation. Under normal physiological conditions, methylation is involved in many functions, including development, suppressing parasitic sequences, silencing incidental promoters, propagating epigenetic inheritance, and marking the inactive X chromosome. In particular, the promoters of many crucial genes contain CG-rich regions called CpG islands. These islands are usually nonmethylated; methylation of these regions results in silencing of the gene's expression. Cancerous (transformed) cells often show hypermethylation of these regions. In transformed cells, methylation of the $O^6$-methylguaninemethyltrasferase (MGMT) enzyme promoter is associated with favorable response to alkylating chemotherapies. These alkylating chemotherapies are often used, along with radiation, in battling glioblastoma multiforme (GBM), a common brain cancer with a dismal (0-5%) survival rate. Methylated cytidines (m5CpG) are therefore important biomarkers for transposable elements, viral DNA, intra-ORF promoter sequences, silenced genes, cancerous tissue and cancer treatment prognoses.

Current methods of evaluating DNA methylation include restriction digests, bisulfite treatment followed by QPCR, sequencing or microarray, and immunoprecipitation or affinity chromatography followed by microarray. The first two approaches are labor intense and technically complicated, and bisulfite treatment is time-consuming. The remaining methods are state-of-the-art, but provide less specific information and are only semi-quantitative. Therefore, in both research and clinical applications, there is need for a rapid, quantitative, and highly specific assay to measure methylation levels while retaining the massive parallelism of microarray technology.

Microarray-formatted DNA methylation assays already exist, but they are inadequate for several reasons. The standard methodology for evaluating microarray hybridization reactions entails incubating a patient's sample for nominally 18 hours and analyzing the DNA-DNA binding results with a single endpoint measurement. This measurement is taken at what is assumed to be the hybridization reaction's equilibrium point. Indeed, there are many thousands of hybridization reactions simultaneously occurring on the microarray—each with its own and different equilibration times, thereby inherently compromising the value of the microarray data. These current microarray-based technologies are also not quantitative, in part because of imperfect molecular recognition (cross-hybridization). This drawback limits their use to tasks such as qualitative (and all too often unreliable) "noisy" screening. Due to these limitations, current microarray techniques attempt to compensate through excessive redundancy. All of these factors have caused the major problem with microarray technology and the genetic problems it has been employed to elucidate—i.e., managing great quantities of inaccurate, irreproducible data. This standard is unacceptable for use in evaluating a patient's DNA for a deadly disease such GBM. Additionally, sorting through copious amounts of typical microarray data profoundly extends analysis time, results in improper conclusions, and initiates interpretive controversy.

Methyl binding domain (MBD) proteins have been shown to recognize methylated DNA both in vitro and in vivo. Recently, protein that binds to symmetrically methylated CpG sites with high affinity and specificity has been engineered by expressing only the methyl binding domain of the protein MBD1.

What is needed in the art are methods and compositions that make use of the MBD protein to analyze methylation of nucleic acids using real time, quantitative assays.

BRIEF SUMMARY OF THE INVENTION

Disclosed herein is a method of detecting methylation of a nucleic acid sample, the method comprising: exposing the nucleic acid sample to an array of oligonucleotide probes; exposing the array of step a) to methyl binding domain (MBD) protein; and detecting interaction between the MBD protein and the nucleic acid sample, wherein interaction indicates that the nucleic acid sample is methylated.

Also disclosed herein is a kit comprising an array of methylated and same sequence non-methylated probes for binding a nucleic acid sample; and MBD protein.

BRIEF DESCRIPTION OF THE DRAWINGS

FIG. 3 shows time sequence of fluorescence images from a typical real-time hybridization experiment (left) and hybridization curves for different target concentrations (right). Synthetic 20-mers were used. The differences in target concentrations are clearly manifested in the time curves. In the case of 10 nM concentration, equilibrium is nearly established. The noise evident in the images and time traces is due to background fluorescence in the glass microscope slide substrate; quartz microscope slides are also utilized as waveguide substrates for which background fluorescence is significantly lower.

MBD only binds symmetrically methylated DNA (here, only in Spot 2); hence, target DNA with an m5CpG site must bind to a probe with an m5CpG in a corresponding position to generate an MBD signal. Fluorescent labels on target DNA are not shown for clarity.

Figure 5:
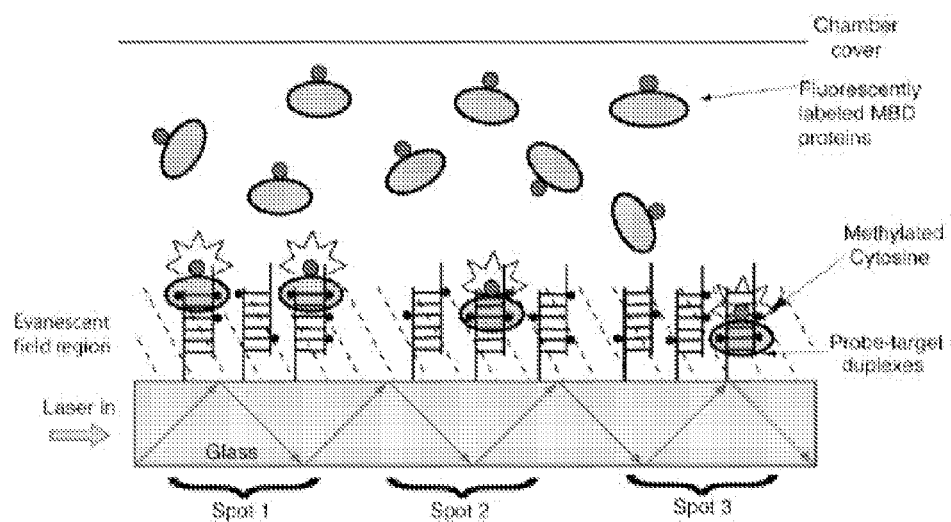

FIG. 5 shows RTM$^3$ for ssDNA of heterogeneous methylation patterns. MBD only binds symmetrically methylated dsDNA; hence, not all dsDNA at each probe spot will bind with MBD. The (calibrated) ratio of MBD to dsDNA fluorescence provides quantitative determination of degree of methylation at each m5CpG site. Fluorescent labels on target DNA not shown for clarity.

Figure 6:
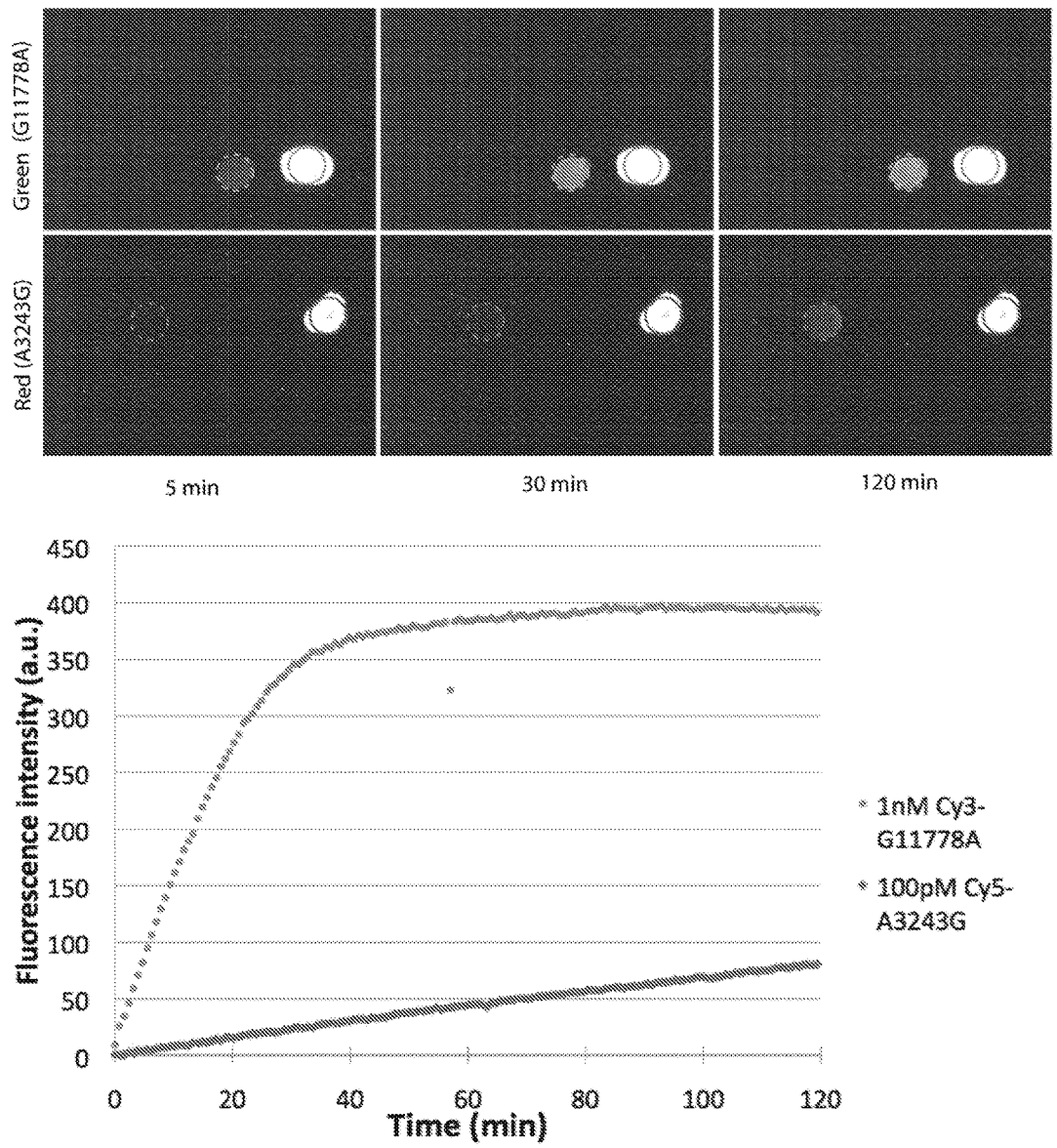

FIG. 6 shows the time sequence of green (upper) and red (lower) raw fluorescence images from a typical two-color real-time hybridization experiment (left) and hybridization curves obtained for the different targets (right). Synthetic 20-mers were used, where each target is at a different concentration and labeled with a different fluorophore (Cy-3 or Cy-5). Probe spots are in dashed outline and the fluorescence from each probe spot grows monotonically with time. Reference spots (solid outlines) are also used in order to calibrate fluorescence from each probe spot; fluorescence from these spots is constant with time. The raw images represent quarter-frames from the camera (i.e. the instrument has the capability to images 100's of spots simultaneously). The hybridization curves were obtained after background subtraction and fluorescence normalization. The difference between the two target concentrations is clearly evident in the relative growth rates. Cross-hybridization between targets and non-matched probes is negligible.

FIG. 7 shows three pairs of DNA targets were annealed outside the biosensor and then captured onto a streptavidin surface. Each was captured at two different surface densities at ~260 RU and 170 RU. Then three samples of MBD were tested for binding across the different target surfaces using a 6 fold dilution of each starting material followed by a 3-fold dilution series. Each dilution series was tested in duplicate.

Figure 8A:
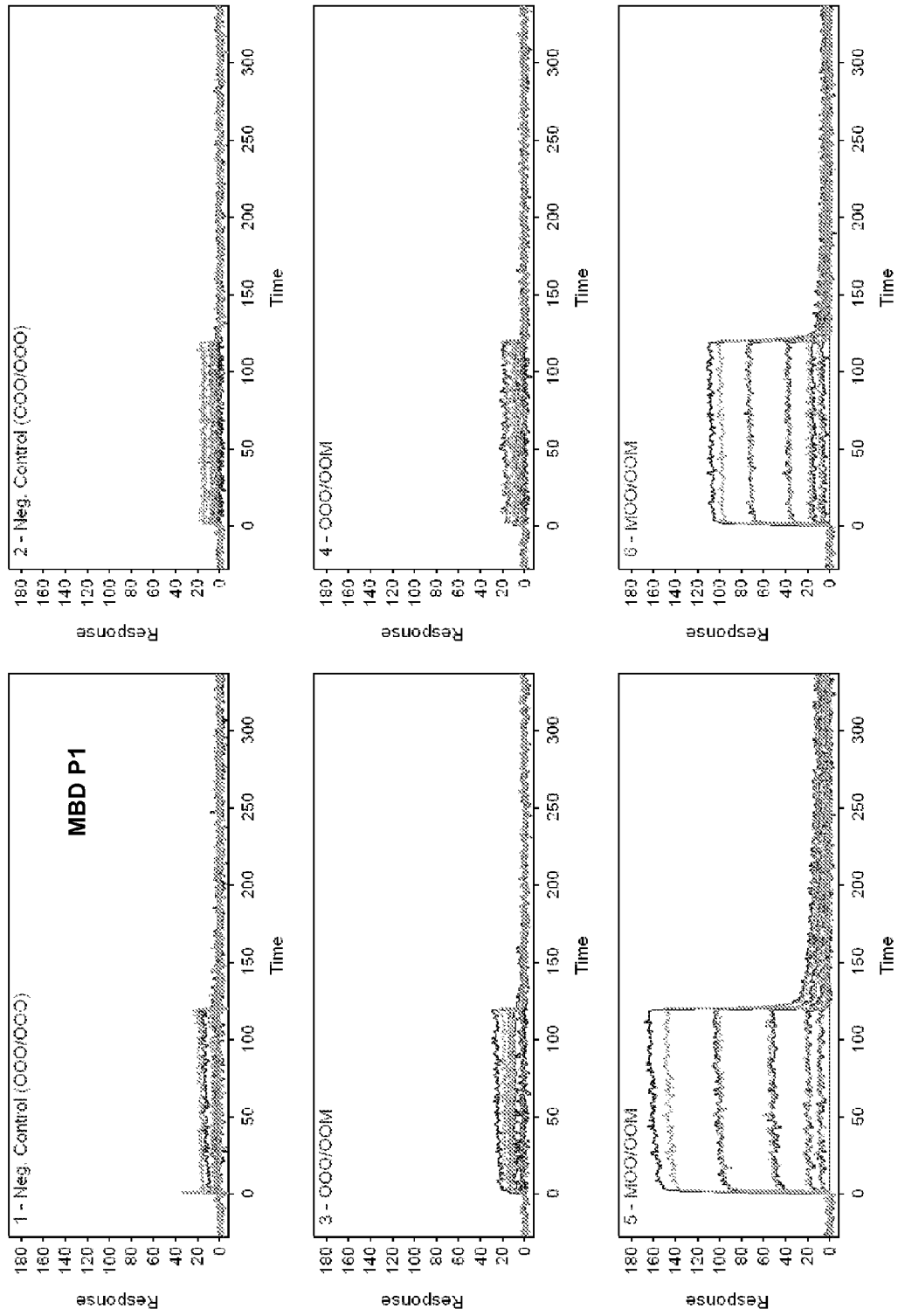
Figure 8B:
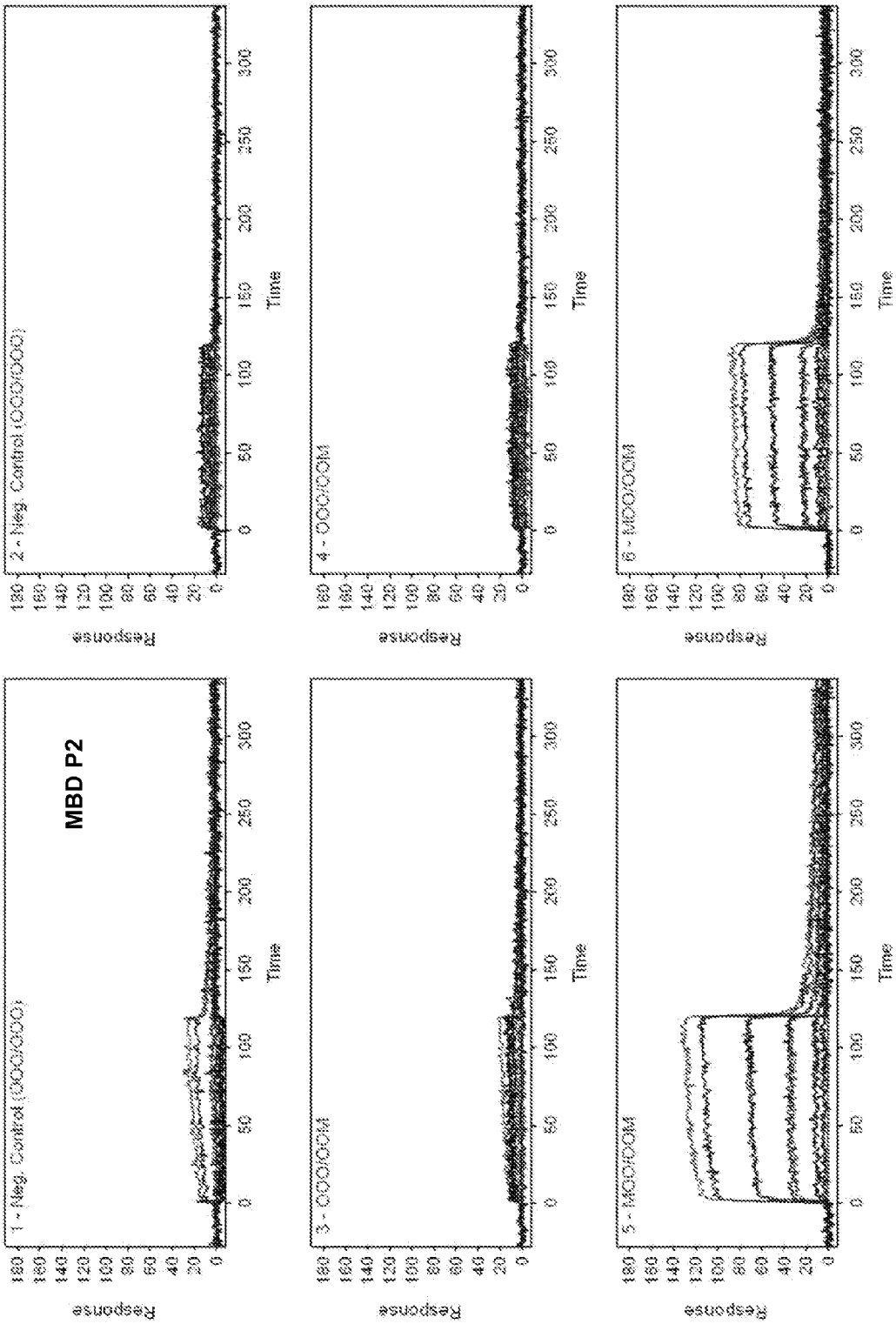
Figure 8C:
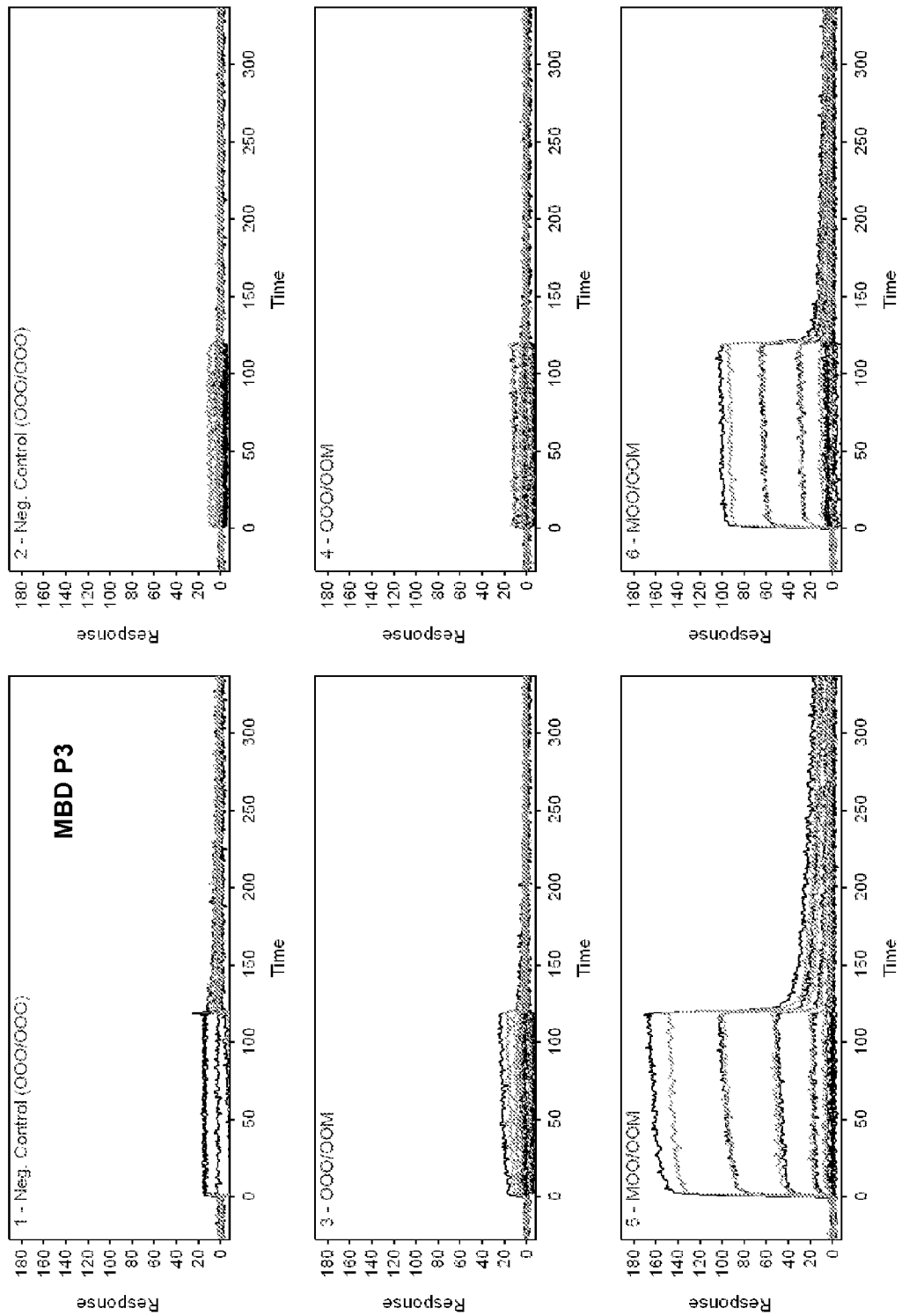

FIGS. 8A-C show the responses for the MBD samples over the different target surfaces. Significant and consistent binding to the MOO/OOM surface with little nonspecific binding was observed.

Figure 9A:
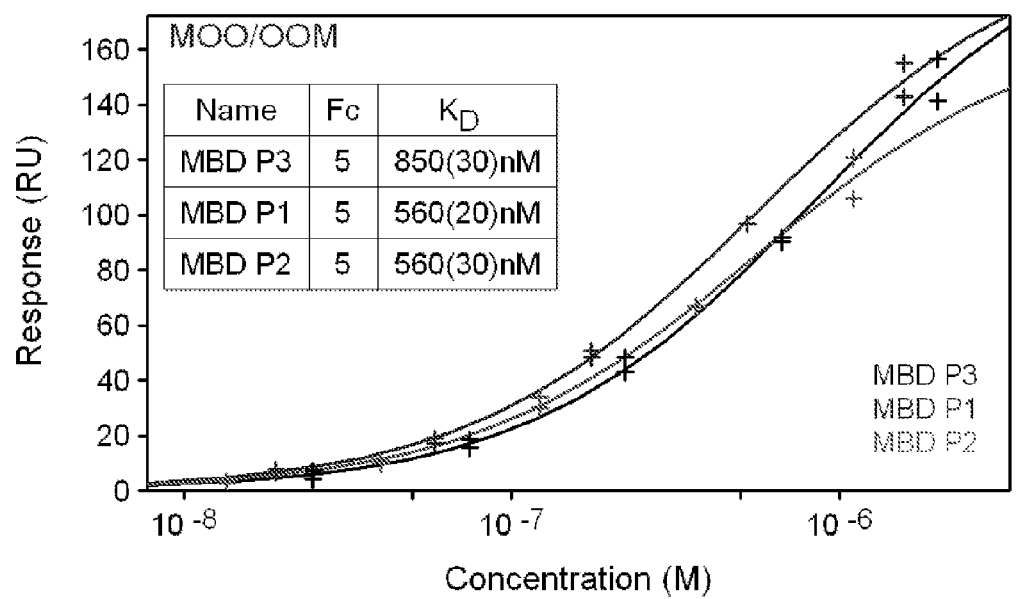
Figure 9B:
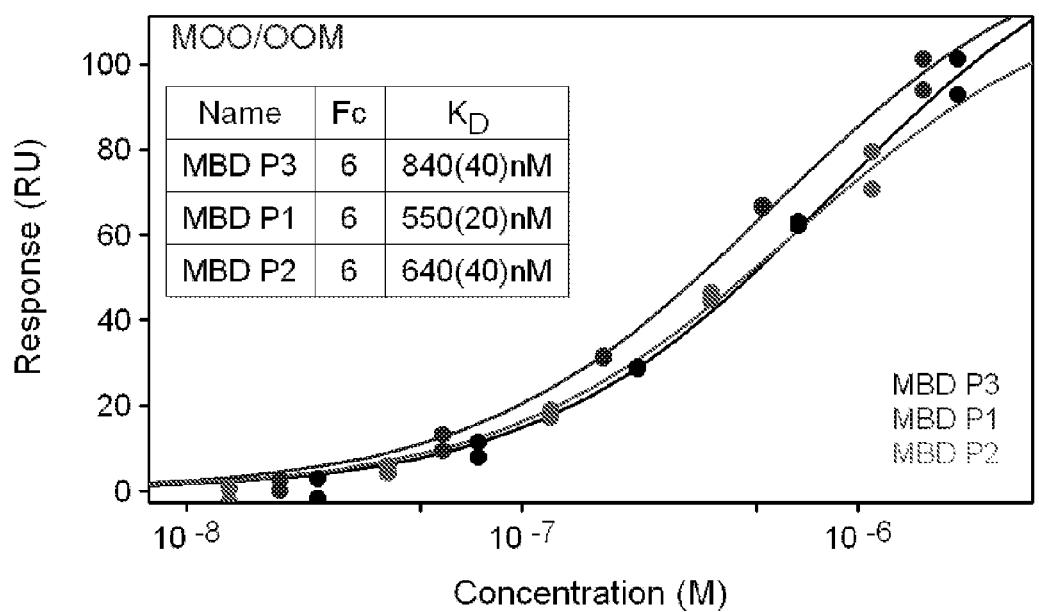

FIGS. 9A-B show fits of the equilibrium response data for the three MBD proteins over the two MOO/OOM target surfaces.

DETAILED DESCRIPTION OF THE INVENTION

Determining the degree of methylation of particular gDNA target regions of interest is useful in many research, diagnostic, medical, forensic, and industrial fields. The methylation of cytosine residues in gDNA is an important epigenetic alteration in eukaryotes. In humans and other mammals methylcytosine is found almost exclusively in cytosine-guanine (CpG) dinucleotides. gDNA methylation plays an important role in gene regulation and changes in methylation patterns are reportedly involved in many human cancers and certain human diseases. Among the earliest and most common genetic alterations observed in human malignancies is the aberrant methylation of CpG islands, particularly CpG islands located within the 5' regulatory regions of genes, causing alterations in the expression of such genes. Subsequently, there is great interest in using DNA methylation markers as diagnostic indicators for early detection, risk assessment, therapeutic evaluation, recurrence monitoring, and the like (see, Widschwendter et al., Clin. Cancer Res. 10:565-71, 2004; Dulaimi et al., Clin. Cancer Res. 10:1887-93, 2004; Topaloglu et al., Clin. Cancer Res. 10:2284-88, 2004; Laird, Nature Reviews, 3:253-266, 2003; Fraga et al., BioTechniques 33:632-49, 2002; Adorjan et al., Nucleic Acids Res. 30(5):e21, 2002; and Colella et al., BioTechniques, 35(1):146-150, 2003). There is also great scientific interest in the role of DNA methylation in embryogenesis, cellular differentiation, transgene expression, transcriptional regulation, and maintenance methylation, among other things.

DEFINITIONS

The term "array" as used herein refers to an intentionally created collection of molecules which can be prepared either synthetically or biosynthetically. The molecules in the array can be identical or different from each other. The array can assume a variety of formats, for example, libraries of soluble molecules; libraries of compounds tethered to resin beads, silica chips, or other solid supports.

The term "complementary" as used herein refers to the hybridization or base pairing between nucleotides or nucleic acids, such as, for instance, between the two strands of a double stranded DNA molecule or between an oligonucleotide primer and a primer binding site on a single stranded nucleic acid to be sequenced or amplified. Complementary nucleotides are, generally, A and T (or A and U), or C and G. Two single stranded RNA or DNA molecules are said to be complementary when the nucleotides of one strand, optimally aligned and compared and with appropriate nucleotide insertions or deletions, pair with at least about 80% of the nucleotides of the other strand, usually at least about 90% to 95%, and more preferably from about 98 to 100%. Perfectly complementary refers to 100% complementarity over the length of a sequence. For example, a 25 base probe is perfectly complementary to a target when all 25 bases of the probe are complementary to a contiguous 25 base sequence of the target with no mismatches between the probe and the target over the length of the probe.

The term "CpG island" as used herein refers to stretches of DNA in a genome that are rich in GC relative to the rest of the genome. Typically the GC content is 50% or greater in these regions which extend over hundreds of base pairs and sometimes thousands. Often these regions mark the 5' ends of genes.

The term "epigenetic" as used herein refers to factors other than the primary sequence of the genome that affect the development or function of an organism, they can affect the phenotype of an organism without changing the genotype. Epigenetic factors include modifications in gene expression that are controlled by heritable but potentially reversible changes in DNA methylation and chromatin structure. Methylation patterns are known to correlate with gene expression and in general highly methylated sequences are poorly expressed.

The term "genome" as used herein is all the genetic material in the chromosomes of an organism. DNA derived from the genetic material in the chromosomes of a particular organism is genomic DNA. A genomic library is a collection of clones made from a set of randomly generated overlapping DNA fragments representing the entire genome of an organism.

The term "hybridization" as used herein refers to the process in which two single-stranded polynucleotides bind non-covalently to form a stable double-stranded polynucleotide; triple-stranded hybridization is also theoretically possible. The resulting (usually) double-stranded polynucleotide is a "hybrid." Hybridizations are usually performed under stringent conditions, for example, at a salt concentration of no more than about 1 M and a temperature of at least 25° C. For example, conditions of 5×SSPE (750 mM NaCl, 50 mM NaPhosphate, 5 mM EDTA, pH 7.4) and a temperature of 25-30° C. are suitable for allele-specific probe hybridizations or conditions of 100 mM MES, 1 M [Na+], 20 mM EDTA, 0.01% Tween-20 and a temperature of 30-50° C., preferably at about 45-50° C. Hybridizations may be performed in the presence of agents such as herring sperm DNA at about 0.1 mg/ml, acetylated BSA at about 0.5 mg/ml. As other factors may affect the stringency of hybridization, including base composition and length of the complementary strands, presence of organic solvents and extent of base mismatching, the combination of parameters is more important than the absolute measure of any one alone. Hybridization conditions suitable for microarrays are described in the Gene Expression Technical Manual, 2004 and the GeneChip Mapping Assay Manual, 2004, available at Affymetrix.com.

The term "hybridization probes" as used herein are oligonucleotides capable of binding in a base-specific manner to a complementary strand of nucleic acid. Such probes include peptide nucleic acids, as described in Nielsen et al., Science 254, 1497-1500 (1991), LNAs, as described in Koshkin et al. Tetrahedron 54:3607-3630, 1998, and U.S. Pat. No. 6,268,490 and other nucleic acid analogs and nucleic acid mimetics.

The term "isolated nucleic acid" as used herein means an object species invention that is the predominant species present (i.e., on a molar basis it is more abundant than any other individual species in the composition). Preferably, an isolated nucleic acid comprises at least about 50, 80 or 90% (on a molar basis) of all macromolecular species present. Most preferably, the object species is purified to essential homogeneity (contaminant species cannot be detected in the composition by conventional detection methods).

The term "mRNA" or sometimes refer by "mRNA transcripts" as used herein, include, but not limited to pre-mRNA transcript(s), transcript processing intermediates, mature mRNA(s) ready for translation and transcripts of the gene or genes, or nucleic acids derived from the mRNA transcript(s). Transcript processing may include splicing, editing and degradation. As used herein, a nucleic acid derived from an mRNA transcript refers to a nucleic acid for whose synthesis the mRNA transcript or a subsequence thereof has ultimately served as a template. Thus, a cDNA reverse transcribed from an mRNA, an RNA transcribed from that cDNA, a DNA amplified from the cDNA, an RNA transcribed from the amplified DNA, etc., are all derived from the mRNA transcript and detection of such derived products is indicative of the presence and/or abundance of the original transcript in a sample. Thus, mRNA derived samples include, but are not limited to, mRNA transcripts of the gene or genes, cDNA reverse transcribed from the mRNA, cRNA transcribed from the cDNA, DNA amplified from the genes, RNA transcribed from amplified DNA, and the like.

The term "nucleic acid" as used herein refers to a polymeric form of nucleotides of any length, either ribonucleotides, deoxyribonucleotides or peptide nucleic acids (PNAs), that comprise purine and pyrimidine bases, or other natural, chemically or biochemically modified, non-natural, or derivatized nucleotide bases. The backbone of the polynucleotide can comprise sugars and phosphate groups, as may typically be found in RNA or DNA, or modified or substituted sugar or phosphate groups. A polynucleotide may comprise modified nucleotides, such as methylated nucleotides and nucleotide analogs. The sequence of nucleotides may be interrupted by non-nucleotide components. Thus the terms nucleoside, nucleotide, deoxynucleoside and deoxynucleotide generally include analogs such as those described herein. These analogs are those molecules having some structural features in common with a naturally occurring nucleoside or nucleotide such that when incorporated into a nucleic acid or oligonucleoside sequence, they allow hybridization with a naturally occurring nucleic acid sequence in solution. Typically, these analogs are derived from naturally occurring nucleosides and nucleotides by replacing and/or modifying the base, the ribose or the phosphodiester moiety. The changes can be tailor made to stabilize or destabilize hybrid formation or enhance the specificity of hybridization with a complementary nucleic acid sequence as desired.

The term "primer" as used herein refers to a single-stranded oligonucleotide capable of acting as a point of initiation for template-directed DNA synthesis under suitable conditions for example, buffer and temperature, in the presence of four different nucleoside triphosphates and an agent for polymerization, such as, for example, DNA or RNA polymerase or reverse transcriptase. The length of the primer, in any given case, depends on, for example, the intended use of the primer, and generally ranges from 15 to 30 nucleotides. Short primer molecules generally require cooler temperatures to form sufficiently stable hybrid complexes with the template. A primer need not reflect the exact sequence of the template but must be sufficiently complementary to hybridize with such template. The primer site is the area of the template to which a primer hybridizes. The primer pair is a set of primers including a 5' upstream primer that hybridizes with the 5' end of the sequence to be amplified and a 3' downstream primer that hybridizes with the complement of the 3' end of the sequence to be amplified.

The term "probe" as used herein refers to a surface-immobilized molecule that can be recognized by a particular target. See U.S. Pat. No. 6,582,908 for an example of arrays having all possible combinations of probes with 10, 12, and more bases. Examples of probes that can be investigated by this invention include, but are not restricted to, agonists and antagonists for cell membrane receptors, toxins and venoms, viral epitopes, hormones (for example, opioid peptides, steroids, etc.), hormone receptors, peptides, enzymes, enzyme substrates, cofactors, drugs, lectins, sugars, oligonucleotides, nucleic acids, oligosaccharides, proteins, and monoclonal antibodies.

The term "solid support", "support", and "substrate" as used herein are used interchangeably and refer to a material or group of materials having a rigid or semi-rigid surface or surfaces. In many embodiments, at least one surface of the solid support will be substantially flat, although in some embodiments it may be desirable to physically separate synthesis regions for different compounds with, for example, wells, raised regions, pins, etched trenches, or the like. According to other embodiments, the solid support(s) will take the form of beads, resins, gels, microspheres, or other geometric configurations. See U.S. Pat. No. 5,744,305 for exemplary substrates.

The term "variant" or "variants" as used herein, refer to polynucleotides or polypeptides that respectively differ in nucleic acid or amino acid composition and/or sequence relative to a reference polynucleotide or polypeptide. Variants may have, but not necessarily, properties of "selective hybridization" relative to the reference polynucleotide or polypeptide.

The term "host cell" as used herein, refers to any biological cell (i.e., for example, animal, mammalian, plant, bacterial, insect, etc) that is capable of transfection by a vector and/or plasmid. A host cell may include, but is not limited to, prokaryotes and eukaryotes.

Embodiments

The methylation of DNA is an important mechanism of epigenetic inheritance, and frequently marks transposons and the promoters of silenced genes. Hypermethylation of cellular DNA usually marks the cell as cancerous; moreover, the methylation level of the MGMT gene promoter in transformed cells is a strong indicator of response to alkylating chemotherapies [hegi05, hermisson06]. Therefore, there is a great need for improved assays to measure the methylation levels of many genetic loci simultaneously. Such assays benefit both research and clinical (i.e. personalized medicine) applications; ideally, an assay is scalable to thousands of loci while utilizing limited sample volumes from human individuals or model organisms.

DNA Methylation

In eukaryotic DNA, cytosine-guanine sequences (CpGs) are often found with the cytosine methylated at carbon 5 (m5C). (The "p" is for the phosphodiester linkage between the nucleotides.) Symmetric methylation of CpG motifs in genomic DNA is a general mechanism of gene silencing and epigenetic inheritance. Indeed, up to 85% of CpGs in exons, transposons, and microsatellies are methylated in normal mammalian cells [bird92, cedar88, lewin98]. It is probable that methylation prevents the expression of parasitic sequences (transposons and viral sequences) and of "accidental" promoter sequences in exons [bird02]. Methylation plays a role in inactivating the X chromosome in female animals [grant88]; it also appears to play a critical role in development [li92, okano99, stancheva00]. However, methylation is a rare event in CG-rich regions of promoters or transcription initiation sequences, which are usually referred to as CpG islands. The situation is significantly different in cancer cells, where massive methylation of promoter regions is frequently observed [esteller01, esteller02]. The latter situation was studied in the context of transcriptional repression of tumor suppressor and DNA repair genes. Correlations between promoter methylation levels and tumorogenesis were established for various types of tumors in different tissues, which makes methylated CpG islands promising biomarkers for diagnosis and prognosis of many cancers [costello00, ordway06, gebhard06a]. This accounts for the numerous model studies and clinical reports on CpG island methylation performed over the last ~15 years.

General Methods

Disclosed herein is a method of detecting methylation of a nucleic acid sample, the method comprising: exposing the nucleic acid sample to an array of oligonucleotide probes; exposing the array of step a) to methyl binding domain (MBD) protein; and detecting interaction between the MBD protein and the nucleic acid sample, wherein interaction indicates that the nucleic acid sample is methylated.

The detection can occur in real time, and can be done quantitatively. The MBD protein can be labeled, or alternatively the sample can be labeled. In yet another embodiment, both the sample and the probe can be labeled. Such labels are known to those of skill in the art and include, but are not limited to, fluorescent labels, scattering labels, and Raman labels.

Fluorophores are compounds or molecules that luminesce. Typically fluorophores absorb electromagnetic energy at one wavelength and emit electromagnetic energy at a second wavelength. A multitude of fluorophores are available that absorb and emit at different wavelengths, allowing for detecting multiple labels in a single sample. Thus, the MBD protein and the sample nucleic acid can both be labeled, e.g., differential labeling. An example of this is two-color labeling, as disclosed herein.

When both the sample and the probe are labeled, they can also be detected using fluorescence resonance energy transfer (FRET) or quenching. Thus, the MDB protein can have a fluorescent label that can be excited by the fluorescent emissions of the fluorophore on the sample. Thus, the MDB protein can have a quencher label that can quench the fluorescent emissions of the fluorophore on the sample. Such detection methods are known to those of skill in the art, and other such combinations of labels are known and contemplated for use herein herein. Quencher labels (and their respective absorption maximums) include, for example, DDQ-I (430 nm), Dabcyl (475 nm), Eclipse (530 nm), Iowa Black FQ (532 nm), BHQ-1 (534 nm), QSY-7 (571 nm), BHQ-2 (580 nm), DDQ-II (630 nm), Iowa Black RQ (630 nm), QSY-21 (660 nm), and BHQ-3 (670 nm).

The MBD protein can be either directly or indirectly linked to the label. For example, the MBD can comprise a His-Tag, wherein the fluorophore or quencher label comprises a metal ion (e.g., nickel or cobalt). Other such indirect labeling methods are known in the art and contemplated for use herein.

In another example, binding of MBD protein can be determined by surface plasmon resonance spectroscopy (SPR).

In order for detection to occur, at least one nucleotide of the oligonucleotide probe can be methylated. The labeled nucleotide can be cytosine in one example. The array can comprise multiple oligonucleotide probes, for example.

The nucleic acid sample can be obtained from a cell, or from tissue such as a tumor. The nucleic acid sample can have complex methylation patterns, and such methylation patterns can be established via methods known to those of skill in the art.

Detecting methylation can be used to detect transformed cells in the sample. This can lead to diagnosis as well as prognosis of the condition of a subject from which the sample was obtained. For example, detecting methylation can be used in determining prognosis. Detecting methylation can also be used to determine treatment. One of skill in the art will appreciate that methylation patterns determine the type and prognosis of various types of cancer, and these results can be used in determining prognosis, diagnosis, and treatment type.

In the methods disclosed herein, interaction between the MBD protein and methylated nucleic acids need not be detecting by enrichment. This is significantly different from those methods currently employed in the art.

The ratio of binding of MBD protein to a single asymmetrically methylated site can be quantified and compared to binding of MBD protein to a symmetrically methylated site within the same sequence context; thereby allowing for accurate calibration of MBD protein binding parameters. This method is discussed further in the examples section.

Also disclosed herein is a kit comprising an array of methylated and same sequence non-methylated probes for binding a nucleic acid sample; and MBD protein. The MBD protein can be labeled, or alternatively the sample can be labeled. In yet another embodiment, both the sample and the probe can be labeled. Such labels are known to those of skill in the art and include, but are not limited to, fluorescent labels, scattering labels, and Raman labels. When both the sample and the probe are labeled, they can be detected using FRET, or quenching. Such detection methods are known to those of skill in the art. The MBD protein and the sample nucleic acid can also both be labeled, such as differential labeling. An example of this is two-color labeling, as disclosed herein. The MBD protein can also comprise a His-Tag in one example. In order for detection to occur, at least one nucleotide of the oligonucleotide probe can be methylated. The labeled nucleotide can be cytosine in one example. The array can comprise multiple oligonucleotide probes, for example.

Methods of Detecting DNA Methylation

Three basic approaches are currently used to assess methylation levels of CpG islands: methylation specific DNA restriction digests [mcclelland85], bisulfite treatment followed by quantitative PCR [herman96, gebhard06b], sequencing [frommer92], or microarray analysis [gebhard06a, gitan02], and enrichment of sample for methylated sequences followed by microarray analysis [keshet06, weber05, rauch06]. Other lesser-used methods exist [e.g. lorente08]. Restriction digests with methylation-sensitive restriction endonucleases are biased and limited according to the palette of restriction enzymes available. These digests serve primarily as a qualitative approach (yes or no answer) based on changes in restriction cleavage sites; the other methods attempt to quantify methylation.

Methylation-specific PCR and the closely related methylation-specific sequencing [frommer92] rely on differences in deamination patterns of methylated and unmethylated cydidines when subjected to bisulfite treatment: unmethylated cytidines undergo deamination to produce a C to U transition, while methylated cytidines are resistant to deamination and are recognized as Cs during polymerization. With the development of the quantitative PCR (QPCR) technique, this approach provides quantitative data on methylation status of the targets. This method, however, has its limitations—namely, it is necessary to perform two amplifications in parallel for each CpG within the sequence of interest (one for unmodified Cs and one for Cs converted to Us). The CpG island of a typical promoter contains hundreds of CpGs; thorough scanning of just one such island could require ~200-1000 separate QPCR reactions. Moreover, for meaningful quantification, the efficiencies of all QPCR reactions must be matched (since corrections made on calculated efficiency differences are not reliable). These limitations can be circumvented by applying a similar methodology for methylation specific sequencing [frommer92]. However, if the sample originates from heterogeneous tissue (as is usually the case with solid tumor biopsies or excisions), results of sequencing are often ambiguous and rarely quantitative. Other bisulfite methods are primarily based upon bisulfite pre-treatment of the sample, followed by hybridization to an array of sequence specific oligonucleotide probes (microarrays). Detection may be either based on fluorescence readout [gebhard06a, gitan02] or mass spectrometric methods [schatz06]. A significant limitation of bisulfite-based approaches is the duration of bisulfite treatment, which usually takes ~16 hours and requires rigorous control for complete deamination.

Recently, a significant amount of attention has been directed towards microarray-based methods of methylation analysis. The capability of microarrays to monitor many genetic loci has been shown to be an efficient screening technique for a large number of targets (up to "whole genome" screening); however, current microarray technology lacks reliable quantitation and require time-consuming preprocessing, both of which limit its usefulness in analytical and clinical applications. Nonetheless, many newer methods of methylation detection use microarrays because of their advantages. These newer methods start by dividing the sample DNA (sheared into appropriately-sized fragments) into two portions. One portion is kept as a reference, while the other is enriched for methylated sequences. In methylated DNA immunoprecipitation (MeDIP), methylated sequences are precipitated by a monoclonal antibody raised against m5C [oakeley97, keshet06, weber05]. The precipitated DNA is extracted and labeled with one fluorescent dye while the unenriched DNA is labeled with another. Both samples are then denatured and hybridized onto a microarray. By comparing the relative intensities of each fluorescent color at each position of the array, the degree of methylation of many genetic loci can be determined semi-quantitatively. A similar technique, the methylated CpG-island recovery assay (MIRA), uses proteins that bind specifically to symmetrically methylated CpG motifs [Rauch06]. These methyl binding domain (MBD) proteins are covalently bound to a solid support (such as Sepharose beads) and packed into a chromatography column. Half of the sample is then enriched by affinity chromatography, i.e. methylated sequences stick to the beads and unmethylated ones do not (essentially a methylated DNA pulldown assay). Elution yields methylation enriched DNA, which is then processed and hybridized along with unenriched DNA as in MeDIP. Although sensitive, MIRA relies on essentially a threshold binding effect and is only semi-quantitative. These limitations motivate the new, more rapid and quantitative method of array-based methylation analysis disclosed herein.

Methyl Binding Domain (MBD) Proteins

Two families of mammalian gene products exhibit specificity in binding to CpG islands of genomic DNAs. One family is represented by proteins containing a methyl binding domain (MBD) and consists of MBD1, MBD2, MBD4 and MeCP2 [meehan89, lewis92, hendrich98] while another one is represented by Kaios proteins with characteristic zinc-finger motif [klose06]. MDB proteins have been investigated extensively of late as part of the mechanism of gene silencing and with regard to their modulation of other chromatin functions (in particular, resistance to DNaseI-dependent removal of nucleosomes) [nan98]. It has been suggested that MBD proteins can be used as an analytical tool for in situ and in vitro detection of symmetrically methylated CpG motifs (m5CpG) in dsDNA. In a recent study, methyl binding proteins were engineered by fusing a purification tag to monomeric or polymeric MBD1 methyl binding domains. Constructs included one to four MBDs in a single polypeptide. These engineered MBD proteins (hereafter referred to merely as MBDs) demonstrate significant specificity of m5CpG recognition (for a single m5CpG motif, $K_d$~30 µM for monomeric MBD and ~0.5 µM for polymeric MBD), showing that MBDs can be used as sensitive analytical tools for detection of methylated CpG islands [jorgensen06]. Moreover, the affinity of MBD binding changes significantly with the number of m5CpG sites in close proximity, which allows quantitative analysis of the level of methylation. The majority of biochemical studies with these MBDs were performed under steady state reaction conditions and analyzed at the end point.

Essentials of Traditional and Real-Time Microarray Technologies

Figure 1:
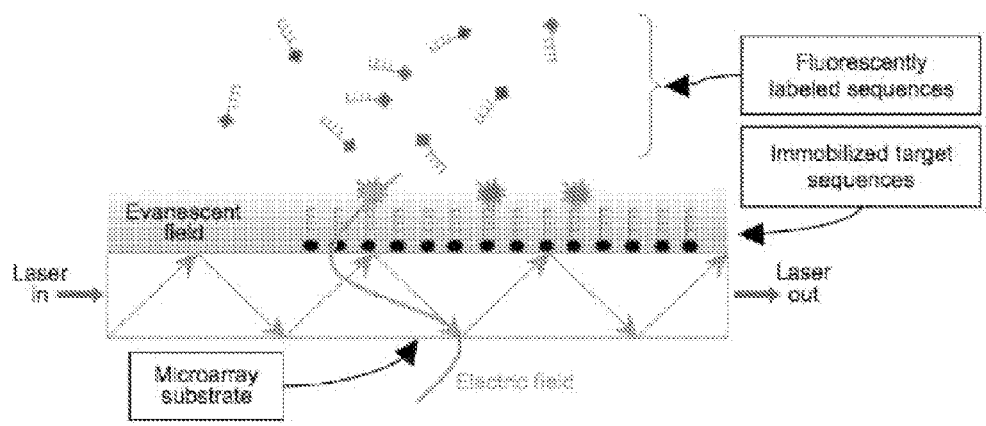
FIG. 1 shows the essentials of DNA microarray technology. Although binding and fluorescence are here shown at the same time, in a traditional microarray, binding takes place first, and fluorescence is only measured after drying and washing the slide. In real time microarrays, binding and fluorescence occur simultaneously, and the substrate doubles as a waveguide.
Figure 2:
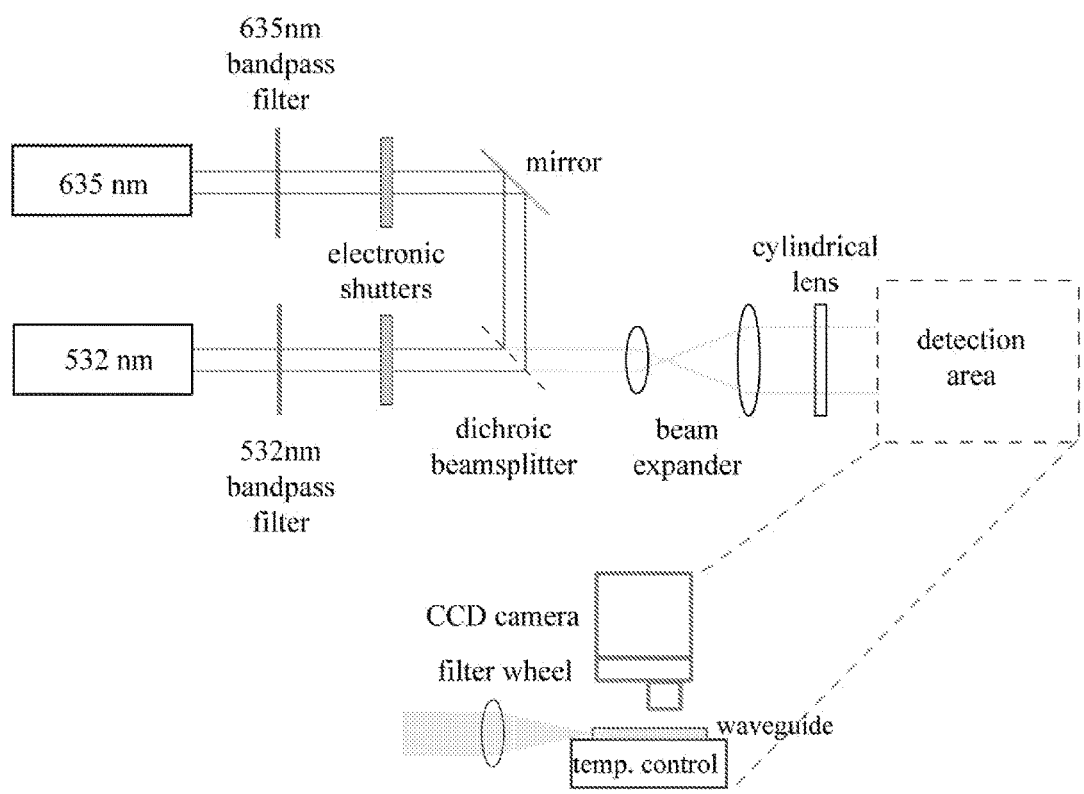
FIG. 2 shows a schematic of the optical setup for the real-time microarray platform. The computer-controlled filter wheel contains optical bandpass filters to pass the fluorescent emission wavelength for the desired fluor while blocking the excitation wavelength. The filter wheel and laser shutters are synchronized to excite the fluor with the appropriate laser.

The essential principles of DNA microarray binding are shown in FIG. 1. Immobilized on the surface are probe oligonucleotides with a complementary sequence to some desired target DNA. A solution of fluorescently labeled sample DNA fills the space above the substrate. When a labeled target meets the correct complementary probe, it is likely that they will bind (hybridize) to form double-stranded (duplex) DNA. The substrate can be divided into many zones (spots), each coated with a different probe. After some length of time, equilibrium is assumed to have occurred, and the slide is dried and washed. The slide is then placed into an array scanner, which excites fluorescence and records its intensity at each position, usually in a serial manner with a microscope objective lens. High-density arrays are now realized in microarray technologies [brown99, heller02], and are the standard for high-throughput DNA studies. Real time microarray technology is similar, except that the substrate doubles as a waveguide and fluorescence occurs at the same time as binding, permitting the hybridization process to be monitored as it happens.

Nucleic acid arrays that are useful in the present invention include those that are commercially available from Affymetrix (Santa Clara, Calif.) under the brand name GeneChip™. Example arrays are shown on the website at affymetrix.com. The present invention contemplates many uses for arrays for methylation analysis. These uses include gene expression monitoring, profiling, library screening, genotyping and diagnostics. Gene expression monitoring and profiling methods can be shown in U.S. Pat. Nos. 5,800,992, 6,013,449, 6,020,135, 6,033,860, 6,040,138, 6,177,248 and 6,309,822. Genotyping and uses therefore are shown in U.S. Ser. Nos. 10/442,021, 10/013,598 (U.S. Patent Application Publication 20030036069), and U.S. Pat. Nos. 5,856,092, 6,300,063, 5,858,659, 6,284,460, 6,361,947, 6,368,799 and 6,333,179. Other uses are embodied in U.S. Pat. Nos. 5,871,928, 5,902,723, 6,045,996, 5,541,061, and 6,197,506.

The present invention also contemplates sample preparation methods in certain preferred embodiments. Prior to or concurrent with hybridization to an array, the sample may be amplified by a variety of mechanisms, some of which may employ PCR. See, for example, PCR Technology: Principles and Applications for DNA Amplification (Ed. H. A. Erlich, Freeman Press, NY, N.Y., 1992); PCR Protocols: A Guide to Methods and Applications (Eds. Innis, et al., Academic Press, San Diego, Calif., 1990); Mattila et al., Nucleic Acids Res. 19, 4967 (1991); Eckert et al., PCR Methods and Applications 1, 17 (1991); PCR (Eds. McPherson et al., IRL Press, Oxford); and U.S. Pat. Nos. 4,683,202, 4,683,195, 4,800,159, 4,965,188, and 5,333,675. The sample may be amplified on the array. See, for example, U.S. Pat. No. 6,300,070 which is incorporated herein by reference.

Additional methods of sample preparation and techniques for reducing the complexity of a nucleic sample are described in Dong et al., Genome Research 11, 1418 (2001), in U.S. Pat. Nos. 6,872,529, 6,361,947, 6,391,592 and 6,107,023, US Patent Publication Nos. 20030096235 and 20030082543 and U.S. patent application Ser. No. 09/916,135.

Methods for conducting polynucleotide hybridization assays have been well developed in the art. Hybridization assay procedures and conditions will vary depending on the application and are selected in accordance with the general binding methods known including those referred to in: Maniatis et al. Molecular Cloning: A Laboratory Manual (2.sup.nd Ed. Cold Spring Harbor, N.Y, 1989); Berger and Kimmel Methods in Enzymology, Vol. 152, Guide to Molecular Cloning Techniques (Academic Press, Inc., San Diego, Calif., 1987); Young and Davism, P.N.A.S, 80: 1194 (1983). Methods and apparatus for carrying out repeated and controlled hybridization reactions have been described in U.S. Pat. Nos. 5,871,928, 5,874,219, 6,045,996 and 6,386,749, 6,391,623 each of which are incorporated herein by reference.

The present invention also contemplates signal detection of hybridization between nucleic acids and a detection agent such as MBDs in certain preferred embodiments. See U.S. Pat. Nos. 5,143,854, 5,578,832; 5,631,734; 5,834,758; 5,936,324; 5,981,956; 6,025,601; 6,141,096; 6,185,030; 6,201,639; 6,218,803; and 6,225,625, in U.S. Ser. No. 10/389,194 and in PCT Application PCT/US99/06097 (published as WO99/47964), each of which also is hereby incorporated by reference in its entirety for all purposes.

Methods and apparatus for signal detection and processing of intensity data are disclosed in, for example, U.S. Pat. Nos. 5,143,854, 5,547,839, 5,578,832, 5,631,734, 5,800,992, 5,834,758; 5,856,092, 5,902,723, 5,936,324, 5,981,956, 6,025,601, 6,090,555, 6,141,096, 6,185,030, 6,201,639; 6,218,803; and 6,225,625, in U.S. Ser. No. 10/389,194, 60/493,495 and in PCT Application PCT/US99/06097 (published as WO 99/47964), each of which also is hereby incorporated by reference in its entirety for all purposes. Instruments and software may also be purchased commercially from various sources, including Affymetrix.

CpG Island Arrays

Mammalian methylation patterns are complex and change during development, see van Steensel and Henikoff Bio-Techniques 35: 346-357 (2003). Methylation in promoter regions is generally accompanied by gene silencing and loss of methylation or loss of the proteins that bind to the methylated CpG can lead to diseases in humans, for example, Immunodeficiency Craniofacial Syndrome and Rett Syndrome, Bestor (2000) Hum. Mol. Genet. 9:2395-2402. DNA methylation may be gene-specific and occurs genome-wide.

Methods for detecting methylation status have been described in, for example U.S. Pat. Nos. 6,214,556, 5,786,146, 6,017,704, 6,265,171, 6,200,756, 6,251,594, 5,912,147, 6,331,393, 6,605,432, and 6,300,071 and US Patent Application publication Nos. 20030148327, 20030148326, 20030143606, 20030082609 and 20050009059, each of which are incorporated herein by reference. Other array based methods of methylation analysis are disclosed in U.S. patent application Ser. No. 11/058,566 (Pg Pub 20050196792 A1) and Ser. No. 11/213,273 (PgPub 20060292585 A1), which are both incorporated herein by reference in their entireties. For a review of some methylation detection methods, see, Oakeley, E. J., Pharmacology & Therapeutics 84:389-400 (1999). Available methods include, but are not limited to: reverse-phase HPLC, thin-layer chromatography, SssI methyltransferases with incorporation of labeled methyl groups, the chloracetaldehyde reaction, differentially sensitive restriction enzymes, hydrazine or permanganate treatment (m5C is cleaved by permanganate treatment but not by hydrazine treatment), sodium bisulfite, combined bisulphate-restriction analysis, and methylation sensitive single nucleotide primer extension.

In a preferred aspect the arrays are used to analyze a sample that has been treated with MBD to differentiate between methylated and unmethylated sequences. Methylation is an epigenetic modification of DNA and information about methylation is typically lost during most methods of nucleic acid amplification such as PCR, random or semi-random priming based amplification, or locus specific primer extension based amplification. However, it has been found that regions that were methylated in a starting sample methods, such as the method may be used that enrich for methylated sequences relative to unmethylated prior to or during amplification, and those enriched sequences may be detected by hybridization to an array (see US Patent Application 2006/0292585).

Significance

Glioblastoma multiforme (GBM) is the most common and most malignant brain tumor in humans, with a survival rate of only 0-5% at five years after presentation, despite therapy. Low-grade astrocytomas (LGA) and oligodendrogliomas have a much better prognosis, but most eventually progress to the higher-grade tumors. The current standard of care for newly diagnosed GBM is surgical resection to the extent feasible, followed by adjuvant radiotherapy. In a recent trial, patients receiving radiotherapy alone had lower survival compared to patients who received radiotherapy plus temozolomide (TMZ) [stupp05]. TMZ and BCNU (1,3-bis (2-chloroethyl)-1-mitrosurea) are methylating/alkylating agents widely used for treatment of GBM [bandres05]. $O^6$-methylguanine DNA methyltransferase (MGMT) is a DNA repair enzyme that (ironically) confers cancer cell resistance to guanine $O^6$-alkylating agent-based chemotherapy. MGMT expression levels are a major predictor of TMZ sensitivity in human glioma cell lines and tumors taken from human patients [hegi05, hermisson06]. In fact, in clinical trials, MGMT gene promoter methylation is correlated with improved survival after combined chemotherapy and radiation [stupp05, vandenbrent06]. There is evidence that methylation of the promoter of the MGMT-gene in even low grade astrocytomas and oligodendrogliomas predicts response to TMZ [neyns05, levin06]. At present, detection of the epigenetic silencing of the MGMT DNA-repair gene by promoter methylation is accomplished by either methylation-specific polymerase chain reaction (PCR) or immunohistochemistry. Both of these processes are time consuming and labor intensive. The disclosed methods provide a more rapid method of detection of MGMT promoter methylation, and can aid in the determination of therapeutic options for patients with malignant gliomas.

The present methods can be used in the detection, diagnosis, prognosis, classification, and treatment of a number of types of cancers. A cancer at any stage of progression can be detected, such as primary, metastatic, and recurrent cancers. Information regarding numerous types of cancer can be found, e.g., from the American Cancer Society (available on the worldwide web at cancer.org), or from, e.g., Harrison's Principles of internal Medicine, Kaspar, et al., eds., 16th Edition, 2005, McGraw-Hill, Inc. Exemplary cancers that can be detected include, e.g., breast cancers, including ductal carcinoma, as well as lung, renal, liver, ovarian, head and neck, thyroid, bladder, cervical, colon, endometrial, esophageal, or prostate cancer or melanoma.

The present invention provides methods for determining whether or not a mammal (e.g., a human) has cancer, i.e., whether or not a biological sample taken from a mammal contains cancerous cells, estimating the risk or likelihood of a mammal developing cancer, classifying cancer types and stages, and monitoring the efficacy of anti-cancer treatment or selecting the appropriate anti-cancer treatment in a mammal with cancer. Such methods are based on the discovery that cancer cells have a different methylation status than normal cells in the DNA regions described in the invention. Accordingly, by determining whether or not a cell contains differentially methylated sequences in the DNA regions as described herein, it is possible to determine whether or not the cell is cancerous.

In numerous embodiments of the present invention, the presence of methylated nucleotides is detected in a biological sample, thereby detecting the presence or absence of cancerous cells in the mammal from which the biological sample was taken. In some embodiments, the biological sample comprises a tissue sample from a tissue suspected of containing cancerous cells. For example, in an individual suspected of having cancer, breast tissue, lymph tissue, lung tissue, brain tissue, or blood can be evaluated. Alternatively, lung, renal, liver, ovarian, head and neck, thyroid, bladder, cervical, colon, endometrial, esophageal, prostate, or skin tissue can be evaluated. The tissue or cells can be obtained by any method known in the art including, e.g., by surgery, biopsy, phlebotomy, swab, nipple discharge, stool, etc. In other embodiments, a tissue sample known to contain cancerous cells, e.g., from a tumor, will be analyzed for the presence or quantity of methylation determine information about the cancer, e.g., the efficacy of certain treatments, the survival expectancy of the individual, etc. In some embodiments, the methods will be used in conjunction with additional diagnostic methods, e.g., detection of other cancer biomarkers, etc.

The methods of the invention can be used to evaluate individuals known or suspected to have cancer or as a routine clinical test, i.e., in an individual not necessarily suspected to have cancer.

Further, the present methods may be used to assess the efficacy of a course of treatment. For example, the efficacy of an anti-cancer treatment can be assessed by monitoring DNA methylation as described herein over time in a mammal having cancer. For example, a reduction or absence of methylation in a biological sample taken from a mammal following a treatment, compared to a level in a sample taken from the mammal before, or earlier in, the treatment, indicates efficacious treatment.

The methods of the present invention can be used to determine the optimal course of treatment in a mammal with cancer. For example, the presence of methylated DNA or an increased quantity of methylation within any of the diagnostic biomarkers can indicate a reduced survival expectancy of a mammal with cancer, thereby indicating a more aggressive treatment for the mammal. In addition, a correlation can be readily established between the presence, absence or quantity of methylation, as described herein, and the relative efficacy of one or another anti-cancer agent. Such analyses can be performed, e.g., retrospectively, i.e., by detecting methylation in one or more of the diagnostic genes in samples taken previously from mammals that have subsequently undergone one or more types of anti-cancer therapy, and correlating the known efficacy of the treatment with the presence, absence or levels of methylation found.

In making a diagnosis, prognosis, risk assessment or classification, in monitoring disease, or in determining the most beneficial course of treatment based on the presence or absence of methylation, the quantity of methylation may be compared to a threshold value that distinguishes between one diagnosis, prognosis, risk assessment, classification, etc., and another. For example, a threshold value can represent the degree of methylation found at a particular DNA region that adequately distinguishes between breast cancer samples and normal breast samples with a desired level of sensitivity and specificity. It is understood that a threshold value will likely vary depending on the assays used to measure methylation, but it is also understood that it is a relatively simple matter to determine a threshold value or range by measuring methylation of a DNA sequence in diseased and normal samples using the particular desired assay and then determining a value that distinguishes at least a majority of the cancer samples from a majority of non-cancer samples.

In some embodiments, threshold values provide at least a specified sensitivity and specificity for detection of a particular cancer type. In some embodiments, the threshold value allows for at least a 50%, 60%, 70%, or 80% sensitivity and specificity for detection of a specific cancer, e.g., breast, lung, renal, liver, ovarian, head and neck, thyroid, bladder, cervical, colon, endometrial, esophageal, prostate cancer or melanoma.

In embodiments involving prognosis of cancer (including, for example, the prediction of progression of non-malignant lesions to invasive carcinoma, prediction of metastasis, prediction of disease recurrance or prediction of a response to a particular treatment), in some embodiments, the threshold value is set such that there is at least 10, 20, 30, 40, 50, 60, 70, 80% or more sensitivity and at least 70% specificity with regard to detecting cancer.

In some embodiments, the methods comprise recording a diagnosis, prognosis, risk assessment or classification, based on the methylation status determined from an individual. Any type of recordation is contemplated, including electronic recordation, e.g., by a computer.

Computer-Based Methods

The calculations for the methods described herein can involve computer-based calculations and tools. For example, a methylation value for a DNA region or portion thereof can be compared by a computer to a threshold value, as described herein. The tools are advantageously provided in the form of computer programs that are executable by a general purpose computer system (referred to herein as a "host computer") of conventional design. The host computer may be configured with many different hardware components and can be made in many dimensions and styles (e.g., desktop PC, laptop, tablet PC, handheld computer, server, workstation, mainframe). Standard components, such as monitors, keyboards, disk drives, CD and/or DVD drives, and the like, may be included. Where the host computer is attached to a network, the connections may be provided via any suitable transport media (e.g., wired, optical, and/or wireless media) and any suitable communication protocol (e.g., TCP/IP); the host computer may include suitable networking hardware (e.g., modem, Ethernet card, WiFi card). The host computer may implement any of a variety of operating systems, including UNIX, Linux, Microsoft Windows, MacOS, or any other operating system.

Computer code for implementing aspects of the present invention may be written in a variety of languages, including PERL, C, C++, Java, JavaScript, VBScript, AWK, or any other scripting or programming language that can be executed on the host computer or that can be compiled to execute on the host computer. Code may also be written or distributed in low level languages such as assembler languages or machine languages.

The host computer system advantageously provides an interface via which the user controls operation of the tools. In the examples described herein, software tools are implemented as scripts (e.g., using PERL), execution of which can be initiated by a user from a standard command line interface of an operating system such as Linux or UNIX. Those skilled in the art will appreciate that commands can be adapted to the operating system as appropriate. In other embodiments, a graphical user interface may be provided, allowing the user to control operations using a pointing device. Thus, the present invention is not limited to any particular user interface.

Scripts or programs incorporating various features of the present invention may be encoded on various computer readable media for storage and/or transmission. Examples of suitable media include magnetic disk or tape, optical storage media such as compact disk (CD) or DVD (digital versatile disk), flash memory, and carrier signals adapted for transmission via wired, optical, and/or wireless networks conforming to a variety of protocols, including the Internet.

The following examples are put forth to provide those of ordinary skill in the art with a complete disclosure and description of how the compositions and/or methods claimed herein are made and evaluated, and are intended to be purely exemplary of the invention and are not intended to limit the scope of what the inventors regard as the invention. Efforts have been made to ensure accuracy with respect to numbers (e.g., amounts, temperature, etc.), but some errors and deviations should be accounted for. The present invention is more particularly described in the following examples which are intended as illustrative only because numerous modifications and variations therein will be apparent to those skilled in the art.

EXAMPLES

Example 1

Methylation Analysis

Real-time hybridization of target to probe is modeled by a single-component, two-compartment reaction. This model has served well in surface plasmon resonance biosensors [myszka98] and in these real-time systems [bishop08]. At each spot, the chemical reaction is described by:

$$\frac{dB(t)}{dt} = k_a C(t)[R_T - B(t)] - k_d B(t)$$

where B(t) corresponds to the surface bound concentration of oligo (i.e. total dsDNA concentration), C(t) is the concentration of the target above the binding spot (where a depletion layer can form) and RT is the total concentration of probes on the surface. C(t) is governed by:

$$\left(\frac{V_i}{S}\right)\frac{dC(t)}{dt} = -k_a C(t)[R_T - B(t)] + k_d B(t) + k_M [C_o - C(t)]$$

where $V_i$ is the volume of the depletion region just above the spot, S is the surface area intersecting the bulk sample solution and depletion region, $C_o$ is the constant bulk solution concentration, and kM represents an effective diffusion rate constant of target across the interface (and is a fitting parameter). In these experiments, this model proved to be an accurate model of microarray hybridization [bishop08] and can be extended to describe binding of MBD proteins.

Figure 4:
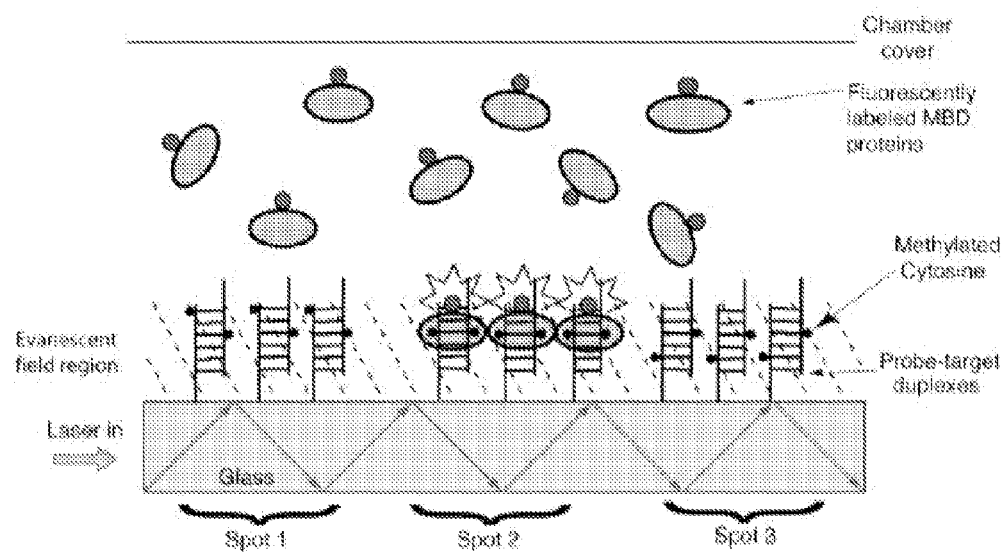
FIG. 4 shows an illustration of the fluorescent MBD binding step. Labels only fluoresce in the evanescent region.

20 to 25-mer oligonucleotides are designed to contain CpG-rich sequences from the MGMT promoter [harris91]. Although such oligos cover little territory across the entire MGMT promoter, short probe sequences have more specific binding to complementary DNA strands, as each base mismatch is more destabilizing than in longer oligos. Chosen secondary structure and dimerization problems at ambient temperatures. Fluorescently labeled oligos with varying sequences of methylated CpG groups serve as synthetic targets; complementary probes are methylated at specific single CpG sites, and are 5'-amino modified for immobilization on GPS-coated microscope slides. Because genetically identical probe sequences have different (single) methylation states located at different spots on the array, target methylation sites can be identified precisely; MBD bind to the symmetrically methylated CpG sites, allowing readout of methylation pattern by observing the signals from a specific subset of spots. (See FIG. 4).

The assay studies are conducted with MBD-GFP fusions. An alternate path is offered by the GST- and His-tagged MBD's. With these MBD's, fluorescence labels can be added via either anti-GST or anti-polyhistidine tag antibodies, respectively. The appropriate plasmids have been obtained to express MBD1 and MBD4. With these plasmids, His-tagged protein can be purified and expressed guided by the methods of Jorgensen et al. [Jorgensen06]. Briefly, the expression vector (with the tagged MBD protein behind an inducible promoter such as T7) is transformed into a suitable *Escherichia coli* expression strain (e.g., BL21(DE)) and expression induced (with IPTG or an appropriate factor). Cells are harvested and lysed (by French press or lysozyme digestion/osmotic shock), and protein is then purified with nickel-NTA resin beads, following the established protocols of the aforementioned authors. Alternately, it may be convenient to express the proteins using retroviral vectors and MBD-deficient mouse embryonic fibroblast cells, as described in a series of publications by Bird [e.g. bird92]. Co-PI Jensen has at his disposal both equipment and expertise for transfection, culturing of either bacterial or human cells, and protein purification. Such purified MBD proteins have been proven to retain methylation specific binding functionality both in vitro and in situ [jorgensen06]. The purified MBD constructs are labeled with Alexa 532 protein labeling kit (Invitrogen), or another suitable dye according to the manufacturers' protocols. Alternatively, labeled anti-his tag protein can be used.

Prior to performing microarray studies, all MBD variants undergo initial testing by binding to symmetrically methylated dsDNA in solution. Running the product on a gel provides solid evidence that binding has occurred (as compared to control experiments). The gel is optically scanned to verify fluorescence from the MBD-dsDNA complexes. During the course of development of the microarray-based RTM3 assay, the different MBD variants are evaluated for their sensitivity and specificity and discuss the results with external consultants. The MBD-GFP fusions perform the best overall, with polymeric fusions showing the greatest sensitivity and MBD1 fusions showing the greatest selectivity.

The substrate for each microarray is a standard quartz microscope slide, 1×3 inches. The organosilane 3-glycidoxypropyltrimethoxysilane (GPS) is used to modify the waveguide surface for covalent attachment of oligonucleotides. The waveguide surface is first cleaned by oxygen plasma for a period of 10 minutes, then placed in a vacuum oven for vapor deposition of GPS for 8 hours. GPS carries an epoxide motif that reacts with the engineered terminal amines on the oligonucleotide probes, covalently immobilizing them on the substrate/waveguide. Spotting of amino-modified oligo probes is accomplished via a home-built hypodermic spotting system that dispenses 100 nL volumes, producing ~250 micron spot diameters. After immobilization, a layer of previously shaped 250 micron thick double-sided VHB tape is affixed (3M brand, part no. 9460PC) This double-sided tape covalently binds to the GPS surface, and is previously micromachined by eximer laser to form a fluidic cavity or channel. After a GPS-coated top slide seals the fluidics, the channel is flushed with 5 mL of hot (50° C.) BSA solution (0.5% in water), followed by 5 mL of 90° C. DI water, to block the surface and tape from nonspecific binding.

At this point the slide assembly (hereafter just "slide") is ready for hybridization. The slide is mounted on a temperature-controlled stage specially designed to accommodate the optics. To excite two different fluors, both a 635 nm (red) diode laser and a 532 nm (or 514 nm or 488 nm) DPSS laser with coaxial paths are used. Total Internal Reflection (TIR, or evanescent) excitation is established by direct end-fire coupling: the laser beams are shaped by lenses into a wide, thin linear profile, then directed straight into the quartz waveguide edge. To avoid photobleaching, lasers are automatically shuttered when not being used.

To start hybridization, buffer solution (0.45 M NaCl, 0.045 M sodium citrate, pH 7.0) is initially pumped through the system to remove air from the channels. Buffer containing target oligonucleotide(s) labeled with a fluorescent dye (Alexa 647) is then driven into the slide chamber by the syringe pump. DNA hybridization then begins. Recall that a target only fluoresces significantly when bound to the surface by a complementary probe; hence, the intensity of a spot's emission indicates the amount of bound target. (FIG. 1.) Positive control spots (surface-bound fluorescent oligos) and negative control spots (oligos not complementary to any target) are included on the same slide. The CCD camera monitors large portions of the slide simultaneously, and is set to acquire fluorescence images at well defined intervals. Images are then analyzed by a program written in Matlab that performs spot identification, background subtraction, and hybridization curve generation for each spot. Hybridization can be monitored until equilibrium is achieved, but this is not necessary. On- and off-rates can then be fitted to hybridization curves; with data from both methylated and non-methylated targets, it can be shown that methylation state does not significantly affect DNA binding kinetics, which manifests in the off rate (note that the off rate can be most accurately determined during the wash step, as described below). On the other hand, if some dependence of hybridization curves on methylation state, then assay development can incorporate kinetic analysis of hybridization, providing additional specificity information when combined with subsequent MBD-based detection. The hybridization data provides information important to interpreting MBD binding in that it allows for the comparison (calibrated) fluorescence of bound DNA (in one color channel) to fluorescence from bound MBD (in the other color channel) to determine methylation load at a specific m5CpG site. After hybridization is complete, the temperature of the slide stage is carefully controlled as the slide is flushed with buffer solution. The cooling curve is optimized to retain legitimate duplexes while discouraging non-specific binding; existing microarray protocols can serve as a starting point. Note that this process is monitored in real-time, allowing quantitative interpretation of dissociation events.

As before, positive control spots (methylated duplex DNA and spots covalently labeled with the same fluor as the MBD) and negative control spots (unmethylated duplex) are included on the slide. The positive and negative controls are important references to determine possible non-specific binding of MBD to nonmethylated targets and to define a normalized scaling of the signal for each of the methylated targets. Images are recorded exactly as before, but using different excitation and emission wavelengths (hence a different laser and optical filters). MBD binding is recorded for each methylation pattern. With the previously recorded knowledge of dsDNA surface concentrations and a known MBD solution concentration, MBD binding can be analyzed using a simple kinetic model detailed below. The dissociation phase is observed under wash conditions (i.e. temperature and buffer stringency) that allow dissociation of the MBD proteins without significant dissociation of the more strongly bound dsDNA. If MBD binding shows minimal sequence specificity as suggested [jorgensen04] standard pre-hybridized control spots can be used in each experiment to have internal standard binding curves of MBD.

Initial studies use a single methylation site per target, so that the kinetic curves can be analyzed by a simple single component kinetic model. For each spot, $$\frac{dB_p(t)}{dt} = k_{a,p} C_p [f \cdot B(t_{hyb}) - B_p(t)] - k_{d,p} B_p(t),$$

where $B_p$ is the surface concentration of bound MBD protein, $C_p$ is protein concentration in bulk solution, $k_{a,p}$ is the protein association constant (on rate), $k_{d,p}$ is the dissociation constant (off rate), and $B(t_{hyb})$ is the surface concentration of oligonucleotide after hybridizing for time $t_{hyb}$. The coefficient f represents the fraction of bound oligonucleotide that has a methylated CpG position that matches that of the probe, or, in other words, f is the methylation load for that specific m5CpG site. The surface concentration of oligo $B(t_{hyb})$, is computed according to the equation:

$$\frac{dB(t)}{dt} = k_a C[R_T - B(t)] - k_d B(t)$$

where C is the concentration of the target in bulk solution, and $R_T$ is the surface concentration of probes. Initially, fitting of the MBD binding curves can be used to determine $k_{a,p}$ and $k_{d,p}$ under conditions of known f. Thereafter, f is the variable solved for, as it indicates the actual methylation state. Note that this set of equations uses the well-mixed assumption, i.e., that solution concentration is the same everywhere. Alternatively, a two-compartment model can be used.

A real time MBD-based microarray methylation (RTM³) assay takes place in two steps. First, a DNA sample containing possibly methylated sequences is hybridized to an array of oligonucleotide probes. Second, this pre-hybridized DNA array is exposed to fluorescently labeled MBD, and the MBD binding to DNA monitored in real time. Appropriate analysis of the binding kinetics of MBD to immobilized targets then provides information on the methylation levels of the target at each addressable spot. As a model system, synthetic oligonucleotides with sequences taken from the promoter region of MGMT can be used. The performance of the assay with oligos of differing genetic and methylation sequences, tested both singly and in combinations, is then performed. Methylation assays covering thousands of loci can be used in clinical settings for diagnosis and personalized treatment.

Synthetic oligonucleotide (oligo) samples homogenous in both sequence and methylation pattern are first tested. The genetic sequence of each oligo is taken from the MGMT promoter region. MBD is obtained as in Jorgensen et al. by overexpression of tagged protein followed by affinity chromatography purification [jorgensen06]. Proof of principle of the assay method is demonstrated by the time required, the sensitivity (i.e., the lowest concentration of oligo or or methylated CpG sites that can be reliably detected), and the specificity (i.e. the frequency of false positives and false negatives). A sensitivity of 0.1 nM or better should be achieved, with false positive/false negative rates of 5% or less. These measurements guide optimization of such factors as fluorescent dye labeling protocol, buffer composition, MBD concentration, and others.

Assay performance can be measured with mixtures of oligos that differ in degree of methylation, sequence of methylation, or genetic sequence. These tests evaluate the accuracy of the method to determine composition.

How the assay performs with DNA targets extracted from human cell cultures can also be measured. Human cell lines with known degrees of methylation at the target sites are available and to the cells are then cultured and their DNA extracted. The extracted genomic DNA contains sequences equivalent to the synthetic oligonucleotides. The DNA is digested with a restriction enzyme cocktail that also excises portions equivalent to the synthetic targets. The assay sample is the digested genomic DNA from one or more cell lines, with no effort made to enrich the fraction of target sequence. The system performance under realistic conditions is therefore elucidated. The known methylation states of the cell strains provide a gross standard for measurement; a subset of samples are verified by bisulfite treatment followed by traditional microarray screening. The cellular samples allow optimization under more complex conditions.

RTM³ can be applied to heterogeneous mixtures of methylation patterns. Defined mixtures of differently methylated targets are exposed to the array, followed by the wash and labeled MBD binding steps. This series of experiments are used to estimate sensitivity limits as well as dynamic ranges of methylation analysis of complex samples. A single target species having multiple methylation sites is tested by measuring binding curves to determine the dependence of MBD affinity with the number of methylated sites (recall that at each probe spot, there can be at most one symmetrically methylated site, but there may be multiple hemimethylated sites).

Heterogeneous mixtures having one genetic sequence, but with several different methylation patterns (as illustrated in FIG. 5) can also be done. Heterogeneous mixtures of multiple unique genetic sequences, starting with one methylated site each, and then mixtures where each sequence has several different methylation patterns are analyzed. Since each mixture has a well-defined and known composition, measurement can be compared with reality in a straightforward manner. Mathematically, error is measured as the root mean square error (RMS), defined here as:

$$RMS = \sqrt{(M_1 - K_1)^2 + (M_2 - K_2)^2 + \ldots (M_n - K_n)^2} = \sqrt{\sum_{n}^{i=1} (M_i - K_i)^2}$$

where $M_1$ is measured fraction of species 1, $M_2$ measured fraction of species 2, et cetera; $K_1$ is known fraction of species 1, et cetera, up to species n. The accuracy is then defined as 1-(RMS). Here, "species" refers to a unique genetic sequence/methylation pattern pair. This metric is used to quantitatively assess the specificity of each MBD variant to just the doubly-methylated site.

Methylation targets based on synthetic oligonucleotides are used to accurately detect methylation status of a given sequence of DNA. RTM$^3$ assay can also be carried out on biopsies or tumor samples as a diagnostic or prognostic tool. Human cell lines can provide a robust source of well-defined DNA that can be exploited. Glioma cell lines T98G and U251 nu/nu demonstrate little change in MGMT expression and are very resistant to alkylating agent-mediated cell death [piper96, natsume05]. However, other glioma cell lines such as AO2, SKMG1, U251SP, and U251MG have a significant amount of MGMT promoter methylation and are sensitive to these same chemotherapeutic agents [natsume05]. By examining genomic DNA from cell lines exhibiting differential MGMT promoter methylation states, the system can be examined under more complex but still controlled conditions. Furthermore, by mixing DNA preps from different lines (MGMT promoter methylated and non-methylated) one can approximate to heterogeneity of DNA extracted from human patient samples. Tissue samples can also be used. DNA can be extracted from normal tissues and from excised tumors and can be evaluated with the RTM$^3$ assay and compared with results from other techniques.

Example 2

Test Binding of MBD Proteins to DNA Targets

Three pairs of DNA targets were annealed outside the biosensor and then captured onto a streptavidin surface. Each was captured at two different surface densities as shown in FIG. 7 at ~260 RU and 170 RU. Then three samples of MBD were tested for binding across the different target surfaces using a 6 fold dilution of each starting material followed by a 3-fold dilution series. Each dilution series was tested in duplicate.

The responses for the MBD samples over the different target surfaces can be seen in FIG. 8. Significant and consistent binding to the MOO/OOM surface with little nonspecific binding was observed. FIG. 9 shows fits of the equilibrium response data for the three MBD proteins over the two MOO/OOM target surfaces.

It is understood that the disclosed invention is not limited to the particular methodology, protocols, and reagents described as these may vary. It is also to be understood that the terminology used herein is for the purpose of describing particular embodiments only, and is not intended to limit the scope of the present invention which will be limited only by the appended claims.

It must be noted that as used herein and in the appended claims, the singular forms "a", "an", and "the" include plural reference unless the context clearly dictates otherwise. Thus, for example, reference to "a host cell" includes a plurality of such host cells, reference to "the antibody" is a reference to one or more antibodies and equivalents thereof known to those skilled in the art, and so forth.

Unless defined otherwise, all technical and scientific terms used herein have the same meanings as commonly understood by one of skill in the art to which the disclosed invention belongs. Although any methods and materials similar or equivalent to those described herein can be used in the practice or testing of the present invention, the preferred methods, devices, and materials are as described. Publications cited herein and the material for which they are cited are specifically incorporated by reference. Nothing herein is to be construed as an admission that the invention is not entitled to antedate such disclosure by virtue of prior invention.

Throughout this application, various publications are referenced. The disclosures of these publications in their entireties are hereby incorporated by reference into this application in order to more fully describe the state of the art to which this pertains.

Although the invention has been described with reference to the presently preferred embodiments, it should be understood that various modifications can be made without departing from the spirit of the invention. Accordingly, the invention is limited only by the following claims.

Throughout this application, various publications are referenced. The disclosures of these publications in their entireties are hereby incorporated by reference into this application in order to more fully describe the state of the art to which this pertains.

Although the invention has been described with reference to the presently preferred embodiments, it should be understood that various modifications can be made without departing from the spirit of the invention. Accordingly, the invention is limited only by the following claims.

REFERENCES

[glioblastoma08] Glioblastoma Multiforme Foundation website, http://gbmfoundation.org/, 2008.

[NCI08] National Cancer Institute website, http://www.cancer.gov/cancertopics/treatment/brain/malignantglioma/print?page=&keyword, 2008.

[market04] Markert, J M, Devita, V T, Hellman, S, Rosenberg, S A., Glioblastoma Multiforme, publ. Jones and Barlett Publishers, Sudbury, Mass., July 2004.

[wikipedia08] Glioblastoma Multiforme in Wikipedia, http://en.wikipedia.org/wiki/Glioblastoma_multiforme, 2008.

[bandres05] Bandres, E., E. Andion, et al. (2005). "Gene expression profile induced by BCNU in human glioma cell lines with differential MGMT expression." J Neurooncol 73(3): 189-98.

[bhanot03] G. Bhanot, Y. Louzoun, J. Zhu, and C. DeLisi. 2003. "The importance of thermodynamic equilibrium for high throughput gene expression arrays". Biophysical Journal 84:124-135.

[bianchi97] N. Bianchi, C. Rustigliano, M. Tomassetti, G. Feriotto, F. Zorzato, and R. Gambari "Biosensor technology and surface plasmon resonance for real-time detection of HIV-1 genomic sequences amplified by polymerase chain reaction," Clinical and Diagnostic Virology 8, 199-208(1997).

[bird92] Bird, A. "The essentials of DNA methylation." Cell 70, 5-8 (1992).

[bird02] Bird, A. "DNA methylation patterns and epigenetic memory" Genes and Development 16, 6-21 (2002).

[bishop06a] Bishop, J., Blair, S., and Chagovetz, A. M. "A competitive kinetic model of nucleic acid surface hybridization in the presence of point mutants". Biophysical Journal 90: 831-840 (2006).

[bishop06b] Bishop, J., Williams, C., Chagovetz, A. M., and Blair, S. "Competitive displacement of DNA during surface hybridization". Biophysical Journal, electronic publication, L10-L12, doi: 10.1529/biophysj.106.097121.

[bishop07] Bishop, J., Chagovetz, A. M., and Blair, S. "Competitive displacement: a sensitive and selective method for the detection of unlabeled molecules". Optics Express 15:4390-4397.

[bishop08] Bishop, J., Chagovetz, A. and Blair, S. "Kinetics of multiplex hybridization: Mechanisms and implications," Biophysical Journal 94, 1726-1734 (2008).

[brown99] P. O. Brown and D. Botstein "Exploring the new work of the genome with DNA microarrays," Nature Genetics 21, 33-37 (1999).

[cedar88] Cedar, H. DNA methylation and gene activity. Cell 53, 3-4 (1988).

[costello00] Costello, J. F., Frühald, M. C., Smiraglia, D. J., Rush, L. J., Robertson, G. P., Gao, X., Wright, F. A., Feramisco, J. D., Peltomäki, P., Lang, J. C., Schuller, D. E., Bloomfield, C. D., Caligiuri, M. A., Yates, A., Nishikawa, R., Su Huang, H.-J., Petrelli, N. J., Zhang, X., O'Dorisio, M. S., Held, W. A., Cavenee, W. K., and Plass, C. "Aberrant CpG-island methylation has non-random and tumour-type-specific patterns". Nature Genetics 24:132-138 (2000).

[esteller01] Esteller, M., Corn, P. G., Baylin, S. B. and Herman, J. G. (2001) A gene hypermethylation profile of human cancer. Cancer Res., 61, 3225±3229.

[esteller02] Esteller, M., Fraga, M. F., Paz, M. F., Campo, E., Colomer, D., Novo, F. J., Calasanz, M. J., Galm, O., Guo, M., Benitez, J. et al. (2002) Cancer epigenetics and methylation. Science, 297, 1807-1808.

[frommer92] Frommer, M., McDonald, L. E., Millar, D. S., Collis, C. M., Watt, F., Grigg, G. W., Molloy, P. L., and Paul, C. L. 1992. A genomic sequencing protocol that yields a positive display of 5-methylcytosine residues in individual DNA strands. Proc. Natl. Acad. Sci. 89: 1827-1831.

[gebhard06a] Gebhard, C., Schwarzfischer, L., Pham, T., Schilling, E., Klug, M., Andreesen, R. and Rehli, M. (2006) Genome-Wide Profiling of CpG Methylation Identifies Novel Targets of Aberrant Hypermethylation in Myeloid Leukemia. Cancer Res., 66, 6118-6128.

[gebhard06b] Gebhard, C, Schwarzfischer, L, Pham, T, Andreesen, R, Mackensen, A and Rehli, M (2006) Rapid and sensitive detection of CpG-methylation using methyl-binding (MB)-PCR, Nucleic Acids Res. 2006 Jul. 5; 34(11):e82.

[gitan02] Gitan, R S, Shi, H, Chuan-Mu, Chen, Yan, P S, and Huang, T H M (2002) Methylation-Specific Oligonucleotide Microarray: A New Potential for High-Throughput Methylation Analysis Genome Research, 12, Issue 1, 158-164.

[grant88] Grant, S. G., and Chapman, V. M. "Mechanisms of X-chromosome regulation". Ann. Rev. Genet. 22:199-233. (1988).

[halperin04] A. Halperin, A. Buhot, and E. B. Zhulina. 2004. Sensitivity, specificity, and the hybridization isotherms of DNA chips. Biophysical Journal 86:718-730.

[halperin06] A. Halperin, A. Buhot, and E. B. Zhulina. 2006. On the hybridization isotherms of DNA microarrays: the Langmuir model and its extensions. Journal Physics: Condensed Matter. 18:S463-S490.

[harris91] Harris, L C, Potter, P M, Tano, K, Shiota, S, Mitra, S, Brent T P (1991) Characterization of the promoter region of the human O6-methylguanine-DNA methyltransferase gene. Nucleic Acids Res. 19(22):6163-7.

[hegi05] Hegi, M. E., A. C. Diserens, et al. (2005). "MGMT gene silencing and benefit from temozolomide in glioblastoma." N Engl J Med 352(10): 997-1003.

[heller02] M. J. Heller "DNA microarray technologies: devices, systems, and applications," Annual Reviews Biomedical Engineering 4, 129-153 (2002).

[hendrich98] Hendrich, B. and Bird, A. (1998) Identification and characterization of a family of mammalian methyl-CpG binding proteins. Mol. Cell. Biol., 18, 6538-6547.

[herman96] Herman, J G, Graff, J R, Myohanen, S, Nelkin, B D, and Baylin, S B (1996) "Methylation-specific PCR: A novel PCR assay for methylation status of CpG islands". Proc. Natl. Acad. Sci. USA, 93, pp. 9821-9826.

[hermisson06] Hermisson, M., A. Klumpp, et al. (2006). "O6-methylguanine DNA methyltransferase and p53 status predict temozolomide sensitivity in human malignant glioma cells." J Neurochem 96(3): 766-76.

[herron93] J. N. Herron, K. D. Caldwell, D. A. Christensen, S. Dyer, V. Hlady, P. Huang, V. Janatova, H.-Wang, and A.-P. Wei, "Fluorescent immunosensors using planar waveguides," in Advances in Fluorescence Sensing Systems vol. SPIE Vol. 1885 28-39 1993.

[jorgensen04]. Jørgensen, H. F., Ben-Porath, I. and Bird, A. P. (2004) "Mbd1 is recruited to both methylated and nonmethylated CpGs via distinct DNA binding domains." Mol. Cell. Biol., 24, 3387-3395.

[jorgensen06] Jørgensen, H, Adie, K, Chaubert, P and Bird, A P "Engineering a high-affinity methyl-CpGbinding protein". Nucleic Acids Research, 2006, 34, No. 13 e96 (2006).

[keshet06] Keshet, I., Schlesinger, Y., Farkash, S., Rand, E., Hecht, M., Segal, E., Pikarski, E., Young, R. A., Niveleau, A., Cedar, H., and Simon, I. "Evidence for an instructive mechanism of de novo methylation in cancer cells". Nature Genetics 38:149-153 (2006).

[klose06] Klose, J P, Bird, A P 2006 Genomic DNA methylation: the mark and its mediators. Trends Biochem Sci. 31(2):89-97. Epub 2006 Jan. 5. Review.

[levin06] Levin, N., I. Lavon, et al. (2006). "Progressive low-grade oligodendrogliomas: response to temozolomide and correlation between genetic profile and O6-methylguanine DNA methyltransferase protein expression." Cancer 106(8): 1759-65.

[lewin98] Lewin, B., Stanley, S. L., Jr and Reed, S. L. (1998) The mystique of epigenetics. Cell, 93, 301-303.

[lewis92] Lewis, J. D., Meehan, R. R., Henzel, W. J., Maurer-Fogy, I., Jeppesen, P., Klein, F. and Bird, A. (1992) Purification, sequence and cellular localisation of a novel chromosomal protein that binds to methylated DNA. Cell, 69, 905-914.

[li92] Li, E., T. H. Bestor, and R. Jaenisch. "Targeted mutation of the DNA methyltransferase gene results in embryonic lethality". Cell 69:915-926. (1992).

[lorente08] Lorente, A., Mueller, W., Urdangarin, E., Lazcoz, P., von Deimling, A., and Castresana, J. S. "Detection of methylation in promoter sequences by melting curve analysis-based semi-quantitative real time PCR". BMC Cancer 8:61 (2008) (pub. ahead of print, doi: 10.1186/1471-2407-8-61).

[meehan89] Meehan, R. R., Lewis, J. D., McKay, S., Kleiner, E. L. and Bird, A. P. (1989) Identification of a mammalian protein that binds specifically to DNA containing methylated CpGs. Cell, 58, 499-507.

[mcclelland85] McClelland, M. and Nelson, M. "The effect of site specific methylation on restriction endonuclease digestion". Nucleic Acids Res. 1985; 13(Suppl): r201-r207.

[myszka98] D. G. Myszka, X. He, M. Dembo, T. A. Morton, and B. Goldstein "Extending the range of rate constants available from BIACORE: interpreting mass transport-influenced binding data," Biophysical Journal 75, 583-594 (1998).

[nan98] Nan, X., Ng, H.-H., Johnson, C. A., Laherty, C. D., Turner, B. M., Eisenman, R. N. and Bird, A. (1998) Transcriptional repression by the methyl-CpG-binding protein MeCP2 involves a histone deacetylase complex. Nature, 393, 386-389.

[natsume05] Natsume, A., D. Ishii, et al. (2005). "IFN-beta down-regulates the expression of DNA repair gene MGMT and sensitizes resistant glioma cells to temozolomide." Cancer Res 65(17): 7573-9.

[neyns05] Neyns, B., J. Sadones, et al. (2005). "The role of chemotherapy in the treatment of low-grade glioma. A review of the literature." Acta Neurol Belg 105(3): 137-43.

[oakeley] Oakleley, E. J., Podesta, A., and Jost, J.-P. "Developmental changes in DNA methylation of the two tobacco pollen nuclei during maturation". Proc. Natl. Acad. Sci. USA 94:11721-11725 (1997).

[Ogino08[ ] Shuji Ogino, Katsuhiko Nosho, Gregory J. Kirkner, Takako Kawasaki, Andrew T. Chan, Eva S. Schernhammer, Edward L. Giovannucci, and Charles S. Fuchs, "A Cohort Study of Tumoral LINE-1 Hypomethylation and Prognosis in Colon Cancer." J Natl Cancer Inst, 3 Dec. 2008; 100: 1734-1738.

[okano99] Okano, M., D. W. Bell, D. A. Haber, and E. Li. "DNA methyltransferases Dnmt3a and Dnmt3b are essential for de novo methylation and mammalian development". Cell 99:247-257, (1999).

[ordway06] J. M. Ordway, J. A. Bedell, R. W. Citek, A. Nunberg, A. Garrido, R. Kendall, J. R. Stevens2, D. Cao, R. W. Doerge, Y. Korshunova, H. Holemon, J. D. McPherson, N. Lakey, J. Leon, R. A. Martienssen and J. A. Jeddeloh. (2006) Comprehensive DNA methylation profiling in a human cancer genome identifies novel epigenetic targets. Carcinogenesis, 2006 December; 27(12): 2409-23. Epub 2006 Sep. 4.

[piper96] Pieper, R. O., S. Patel, et al. (1996). "Methylation of CpG island transcription factor binding sites is unnecessary for aberrant silencing of the human MGMT gene." J Biol Chem 271(23): 13916-24.

[plowman96] T. E. Plowman, W. M. Reichert, C. R. Peters, H. K. Wang, D. A. Christensen, and J. N. Herron "Femtomolar sensitivity using a channel-etched thin film waveguide fluoroimmunosensor," Biosensors and Bioelectronics 11, 149-160 (1996).

[rausch06] Rauch, T., Li, H., Wu, X., and Pfeifer, G. P. "MIRA-Assisted Microarray Analysis, a New Technology for the Determination of DNA Methylation Patterns, Identifies Frequent Methylation of Homeodomain-Containing Genes in Lung Cancer Cells". Cancer Research 66, 7939-7947 (2006).

[schatz06] Schatz P, Distler J, Berlin K, and Schuster M Novel method for high throughput DNA methylation marker evaluation using PNA-probe library hybridization and MALDI-TOF detection Nucleic Acids Res. 2006 May 2; 34(8):e59.

[stancheva00] Stancheva, I., and R. R. Meehan. "Transient depletion of xDnmt1 leads to premature gene activation in Xenopus embryos". Genes Dev. 14:313-327 (2000).

[stupp05] Stupp, R., W. P. Mason, et al. (2005). "Radiotherapy plus concomitant and adjuvant temozolomide for glioblastoma." N Engl J Med 352(10): 987-96.

[Surawicz98] Surawicz, T S, Davis, F, Freels, S, Laws, E R, Menck, J R, "Brain tumor survival: Results from the National Cancer Data Base". J of Neuro-Oncology, 40(2), 151-160, (1998).

[vandenbrent06] van den Bent, M. J., M. E. Hegi, et al. (2006). "Recent developments in the use of chemotherapy in brain tumours." Eur J Cancer 42(5): 582-8.

[weber05] Weber, M., Davies, J. J., Wittig, D., Oakeley, E. J., Haase, M., Lam, W. L., and Schübeler, D. "Chromosome-wide and promoter-specific analyses identify sites of differential DNA methylation in normal and transformed human cells". Nature Genetics 37, 853-862 (2005).

[zhou91] Y. Zhou, P. J. Laybourn, J. V. Magill, and R. M. D. L. Rue "An evanescent fluorescence biosensor using ion-exchanged buried waveguides and the enhancement of peak fluorescence," Biosensors and Bioelectronics 6, 595-607 (1991).

We claim:

1. A method of detecting methylation of a nucleic acid sample, the method comprising:
  a. exposing the nucleic acid sample to an array of oligonucleotide probes coupled to a solid substrate to form double-stranded duplexes;
  b. exposing the array of step a) to methyl binding domain (MBD) protein; and
  c. detecting interaction between the MBD protein and the double-stranded duplexes, wherein interaction indicates that the double-stranded duplexes are methylated.

2. The method of claim 1, wherein detection occurs in real time.

3. The method of claim 1, wherein detecting methylation is done quantitatively.

4. The method of claim 1, wherein the MBD protein is labeled.

5. The method of claim 1, wherein the sample is labeled.

6. The method of claim 5, wherein the probe is also labeled.

7. The method of claim 6, wherein the probe and sample are detected by FRET or quenching.

8. The method of claim 1, wherein the MBD protein comprises a His-Tag.

9. The method of claim 1, wherein binding of MBD protein is determined by surface plasmon resonance spectroscopy (SPR).

10. The method of claim 1, wherein at least one nucleotide of the oligonucleotide probe is methylated.

11. The method of claim 1, wherein the nucleic acid sample is from a tumor.

12. The method of claim 1, wherein the nucleic acid sample has complex methylation patterns.

13. The method of claim 1, wherein detecting methylation is used to detect transformed cells in the sample.

14. The method of claim 11, wherein detecting methylation is used in determining prognosis.

15. The method of claim 11, wherein detecting methylation is used to determine treatment.

16. The method of claim 1, wherein interaction between the MBD protein and methylated nucleic acids is not determined by enrichment.

17. The method of claim 1, wherein the ratio of binding of MBD protein to a single asymmetrically methylated site can be quantified and compared to binding of MBD protein to a symmetrically methylated site within the same sequence context; thereby allowing for accurate calibration of MBD protein binding parameters.

18. The method of claim 4, wherein the labeled MBD protein is an MBD-GFP fusion protein.

* * * * *